US008652813B2

(12) United States Patent
Baidyaroy et al.

(10) Patent No.: US 8,652,813 B2
(45) Date of Patent: Feb. 18, 2014

(54) **RECOMBINANT *THERMOASCUS AURANTIACUS* β-GLUCOSIDASE VARIANTS**

(75) Inventors: Dipnath Baidyaroy, Fremont, CA (US); Louis Clark, San Francisco, CA (US); Lisa M. Newman, San Jose, CA (US)

(73) Assignee: Codexis, Inc., Redwood City, CA (US)

( * ) Notice: Subject to any disclaimer, the term of this patent is extended or adjusted under 35 U.S.C. 154(b) by 68 days.

(21) Appl. No.: 12/950,150

(22) Filed: Nov. 19, 2010

(65) Prior Publication Data

US 2011/0124058 A1 May 26, 2011

Related U.S. Application Data

(60) Provisional application No. 61/264,605, filed on Nov. 25, 2009.

(51) Int. Cl.
*C12P 19/02* (2006.01)

(52) U.S. Cl.
USPC .......... 435/105; 435/7.1; 435/320.1; 435/325

(58) Field of Classification Search
None
See application file for complete search history.

(56) References Cited

U.S. PATENT DOCUMENTS

| | | | |
|---|---|---|---|
| 4,486,553 A | 12/1984 | Wesch | |
| 5,648,263 A | 7/1997 | Schulein et al. | |
| 5,811,381 A | 9/1998 | Emalfarb et al. | |
| 6,015,707 A | 1/2000 | Emalfarb et al. | |
| 6,573,086 B1 | 6/2003 | Emalfrab et al. | |
| 7,244,605 B2 | 7/2007 | Harris et al. | |
| 7,413,888 B2* | 8/2008 | Fidantsef et al. | 435/209 |
| 7,638,616 B2* | 12/2009 | Fidantsef et al. | 536/23.2 |
| 7,696,411 B2 | 4/2010 | Sticklen et al. | |
| 7,783,428 B2 | 8/2010 | Gustafsson et al. | |
| 7,883,872 B2 | 2/2011 | Gusakov et al. | |
| 7,884,066 B2* | 2/2011 | Ting | 514/1.1 |
| 7,884,069 B2* | 2/2011 | Schaebitz et al. | 424/85.1 |
| 7,884,263 B2* | 2/2011 | Dewey et al. | 800/285 |
| 2008/0057541 A1 | 3/2008 | Hill et al. | |
| 2008/0194005 A1 | 8/2008 | Emalfarb et al. | |
| 2009/0042266 A1 | 2/2009 | Vehmaanpera et al. | |
| 2009/0053765 A1 | 2/2009 | Fidansev et al. | |
| 2009/0061484 A1 | 3/2009 | Scott et al. | |
| 2009/0099079 A1 | 4/2009 | Emalfarb et al. | |
| 2009/0209009 A1 | 8/2009 | Tolan et al. | |
| 2011/0124058 A1* | 5/2011 | Baidyaroy et al. | 435/105 |

FOREIGN PATENT DOCUMENTS

| | | | |
|---|---|---|---|
| EP | 137280 B1 | 3/1992 | |
| WO | 95/22625 A1 | 8/1995 | |
| WO | 96/00787 A1 | 1/1996 | |
| WO | 97/35966 A1 | 10/1997 | |
| WO | 98/15633 A1 | 4/1998 | |
| WO | 98/27230 A1 | 6/1998 | |
| WO | 98/31821 A2 | 7/1998 | |
| WO | 01/75767 A2 | 10/2001 | |
| WO | 03/075129 A2 | 9/2003 | |
| WO | 2004/048592 A2 | 6/2004 | |
| WO | 2007/075899 A2 | 7/2007 | |
| WO | 2008/073914 A2 | 6/2008 | |

OTHER PUBLICATIONS

Latham (Am. J. Hum. Genet.vol. 47, pp. 79-86, 1990.*
Adams, S.P., et al., "Hindered Dialkylamino Nucleoside Phosphite Reagents in the Synthesis of Two DNA 51-Mers," J. Am. Chem. Soc., 105:661-663, 1983.
Altschul, S., et al., "Gapped BLAST and PSI-BLAST: a new generation of protein database search programs," Nucleic Acids Res., 25(17):3389-3402, 1997.
Beaucage, S.L., et al., "Deoxynucleoside phosphoramidites—A new class of key intermediates for deoxypolynucleotide synthesis," Tetrahed. Lett., 22:1859-69, 1981.
Bhatia, Y., et al., "Microbial beta-glucosidases: cloning, properties, and applications," Crit Rev Biotechnol., 22(4): 375-407, 2002.
Blaiseau, P.-L., et al., "Primary structure of a chitinase-encoding gene (chi1) from the filamentous fungus Aphanocladium album: similarity to bacterial chitinases," Gene, 120(2):243-248, 1992.
Boel, E., et al., "Two different types of intervening sequences in the glucoamylase gene from *Aspergillus niger*," EMBO J., 3(7):1581-85, 1984.
Botstein, D., et al., "Strategies and applications of in vitro mutagenesis," Science, 229(4719):1193-1201, 1985.
Breves, R., et al., "Genes encoding two different beta-glucosidases of *Thermoanaerobacter brockii* are clustered in a common operon," Appl. Environ. Microbiol,. 63(10):3902-3910, 1997.
Carter, P., "Site-directed mutagenesis," Biochem. J., 237:1-7, 1986.
Caruthers, M.H., et al., "Chemical Synthesis and Biological Studies on Mutated Gene-control Regions," Cold Spring Harbor Symp. Quant. Biol., 47:411-18, 1982.
Case, M.E., et al., "Efficient Transformation of *Neurospora crassa* by Utilizing Hybrid Plasmid DNA," Proc. Natl. Acad. Sci. USA, 76(10):5259-5263, 1979.
Christians, F.C., et al., "Directed evolution of thymidine kinase for AZT phosphorylation using DNA family shuffling," Nat. Biotechnol., 17:259-264, 1999.
Crameri, A., et al., "DNA shuffling of a family of genes from diverse species accelerates directed evolution," Nature, 391(6664):288-291,1998.
Crameri, A., et al., "Improved green fluorescent protein by molecular evolution using DNA shuffling," Nat. Biotechnol., 14(3):315-319, 1996.
Crameri, A., et al., "Molecular evolution of an arsenate detoxification pathway by DNA shuffling," Nat. Biotechnol., 15(5):436-438, 1997.
Dale, S.J. et al., "Oligonucleotide-directed random mutagenesis using the phosphorothioate method," Methods Mol. Biol., 57:369-74, 1996.

(Continued)

*Primary Examiner* — Hope Robinson
(74) *Attorney, Agent, or Firm* — Codexis, Inc.

(57) ABSTRACT

The present invention provides compositions and methods for the expression of recombinant β-glucosidase variants, as well as their use in the production of fermentable sugars from cellulosic biomass.

6 Claims, 1 Drawing Sheet

(56) References Cited

OTHER PUBLICATIONS

Dayhoff, M.O., et al., "A model of evolutionary change in proteins," Atlas Prot. Seq. Struct., 5(Suppl. 3):345-352, 1978.
Fox, R., "Directed molecular evolution by machine learning and the influence of nonlinear interactions," J. Theor. Biol., 234(2):187-199, 2005.
Fox, R., et al., "Optimizing the search algorithm for protein engineering by directed evolution," Protein Eng., 16(8):589-597, 2003.
Henaut, A., et al., "Analysis and Predictions from *Escherichia coli* Sequences, or *E. coli* In Silico," *Escherichia coli* and *Salmonella*, ASM Press, Washington D.C., [1996], pp. 2047-2066.
Henikoff, S., et al., "Amino acid substitution matrices from protein blocks," Proc. Natl. Acad. Sci., 89:10915-10919, 1992.
Henriksen, A.L.S., et al., "Study of the glucoamylase promoter in *Aspergillus niger* using green fluorescent protein," Microbiol., 145:729-34, 1999.
Hong, J., et al., "Cloning and functional expression of thermostable beta-glucosidase gene from *Thermoascus aurantiacus*," Appl. Environ. Microbiol., 73:1331-1339, 2007.
Hong, J., et al., "Construction of thermotolerant yeast expressing thermostable cellulase genes," J. Biotechnol., 130:114-23, 2007.
Johnstone, I.L., et al., "Cloning an *Aspergillus nidulans* developmental gene by transformation," EMBO J., 4(5):1307-1311, 1985.
Kelly, J.M., et al., "Transformation of *Aspergillus niger* by the amdS gene of *Aspergillus nidulans*," EMBO J., 4(2):475-479, 1985.
Kinsey, J.A., et al., "Transformation of *Neurospora crassa* with the cloned am (glutamate dehydrogenase) gene," Mol. Cell. Biol., 4:117-122, 1984.
Kramer, B., et al., "Different base/base mismatches are corrected with different efficiencies by the methyl-directed Dna mismatch-repair system of *E. coli*," Cell, 38(3):879-887, 1984.
Ladisch, M.R., et al., "Process considerations in the enzymatic hydrolysis of biomass," Enz. Microb. Technol., 5:82-102, 1983.
Limon, M.C., et al., "Primary structure and expression pattern of the 33-kDa chitinase gene from the mycoparasitic fungus *Trichoderma harzianum*," Curr. Genet., 28:478-83, 1995.
Ling, M., et al., "Approaches to DNA Mutagenesis:An Overview," Anal. Biochem., 254:157-78, 1999.
Mase, T., et al., "Purification, characterization, and a potential application of beta-gludosidase from *Asperfillus pulverulentus* YM-80," J. Appl. Glycosci., 51:211-216, 2004.
Matthes, H., et al., "Simultaneous rapid chemical synthesis of over one hundred oligonucleotides on a microscale," Embo J. 3(4):801-05, 1984.
McInerney, J.O., "GCUA: general codon usage analysis," Bioinformatics, 14(4):372-73, 1998.
Minshull, J., et al., "Protein evolution by molecular breeding," Curr. Op. Chem. Biol., 3(3):284-290, 1999.
Mount, D.A., "Bioinformatics: Sequence and Genome Analysis," Cold Spring Harbor Laboratory Press, Cold Spring Harbor, N.Y., Chapter 8, pp. 337-379, 2001.
Murray, P., et al., "Expression in *Trichoderma reesei* and characterization of a thermostable family 3 beta-glucosidase from the moderately thermophilic fungus Talaromyces emersonil," Prot. Expr. Purif., 38(2):248-257, 2004.
Nakamura, Y., et al., "Codon usage tabulated from international DNA sequence databases: status for the year 2000," Nucl. Acids Res., 28:292, 2000.
Nunberg, J.H., et al., "Molecular cloning and characterization of the glucoamylase gene of *Aspergillus awamori*," Mol. Cell Biol., 4(11):2306-2315, 1984.

Park, J.B., et al., "The human glutaredoxin gene: determination of its organization, transcription start point, and promoter analysis," Gene, 197:189-93, 1997.
Parry, N.J., et al., "Biochemical characterization and mechanism of action of a thermostable beta-glucosidase purified from *Thermoascus aurantiacus*," Biochem. J., 353:117-127, 2001.
Porath, J., "Immobilized metal ion affinity chromatography," Prot. Express. Purific., 3:263-281, 1992.
Romanos, M.A., et al., "Foreign gene expression in yeast: a review," Yeast 8:423-488, 1992.
Sabin, E.A., et al., "High-level expression and in vivo processing of chimeric ubiquitin fusion proteins in *Saccharomyces cerevisiae*," BioTechnol., 7:705-709, 1989.
Sheir-Neiss, G., et al., "Characterization of the secreted cellulases of *Trichoderma reesei* wild type and mutants during controlled fermentations," Appl. Microbiol. Biotechnol., 20:46-53, 1984.
Simonen, M., et al., "Protein secretion in *Bacillus* species," Microbiol. Rev., 57: 109-137, 1993.
Smith, M., "In vitro mutagenesis," Ann. Rev. Genet., 19:423-462, 1985.
Stemmer, W., "DNA shuffling by random fragmentation and reassembly: In vitro recombination for molecular evolution," Proc. Nat. Acad. Sci., U.S.A., 91:10747-10751, 1994.
Stemmer, W., "Rapid evolution of a protein in vitro by DNA shuffling," Nature, 370(6488):389-391, 1994.
Stenico, M., et al., "Codon usage in *Caenorhabditis elegans*: delineation of translational selection and mutational biases," Nucl. Acids Res., 22(13):2437-46, 1994.
Taussig, R., et al., "Nucleotide sequence of the yeast SUC2 gene for invertase," Nucl. Acids Res., 11(6):1943-54, 1983.
Tilburn, J., et al., "Transformation by integration in *Aspergillus nidulans*," Gene, 26(2-3):205-221, 1982.
Tiwari, S., et al., "Prediction of probable genes by Fourier analysis of genomic sequences," Comput. Appl. Biosci., 13(3):263-270, 1997.
Uberbacher, E.C., et al., "Discovering and Understanding Genes in Human DNA Sequence Using GRAIL," Meth. Enzymol., 266:259-281, 1996.
Viikari, L., et al., "Thermostable enzymes in lignocellulose hydrolysis," Adv. Biochem. Eng. Biotechnol., 108:121-45, 2007.
Wada, K., et al., "Codon usage tabulated from the GenBank genetic sequence data," Nucl. Acids Res., 20:2111-2118, 1992.
Wells, J.A., et al., "Cassette mutagenesis: an efficient method for generation of multiple mutations at defined sites," Gene, 34:315-323, 1985.
Wilson, I.A., et al., "The structure of an antigenic determinant in a protein," Cell, 37:767-78, 1984.
Wright, A., et al., "Diverse plasmid DNA vectors by directed molecular evolution of cytomegalovirus promoters," Hum. Gene Ther., 16(7):881-892, 2005.
Wright, F., "The 'effective number of codons' used in a gene," Gene, 87:23-29, 1990.
Yanai, T., et al., "Isolation and Properties of Beta-Glucosidase Produced by *Debaryomyces hansenii* and Its Application in Winemaking," Am. J. Enol. Eitic., 50(3):231-235, 1999.
Yelton, M.M., et al., "Transformation of *Aspergillus nidulans* by Using a trpC Plasmid," Proc. Natl. Acad. Sci. USA, 81:1470-1474, 1984.
Zhang, J-H., et al., "Directed evolution of a fucosidase from a galactosidase by DNA shuffling and screening," Proc. Nat. Acad. Sci., U.S.A., 94:4504-4509, 1997.
Zhu, T., et al., "Construction of two Gateway vectors for gene expression in fungi," Plasmid 62:128-33, 2009.

\* cited by examiner

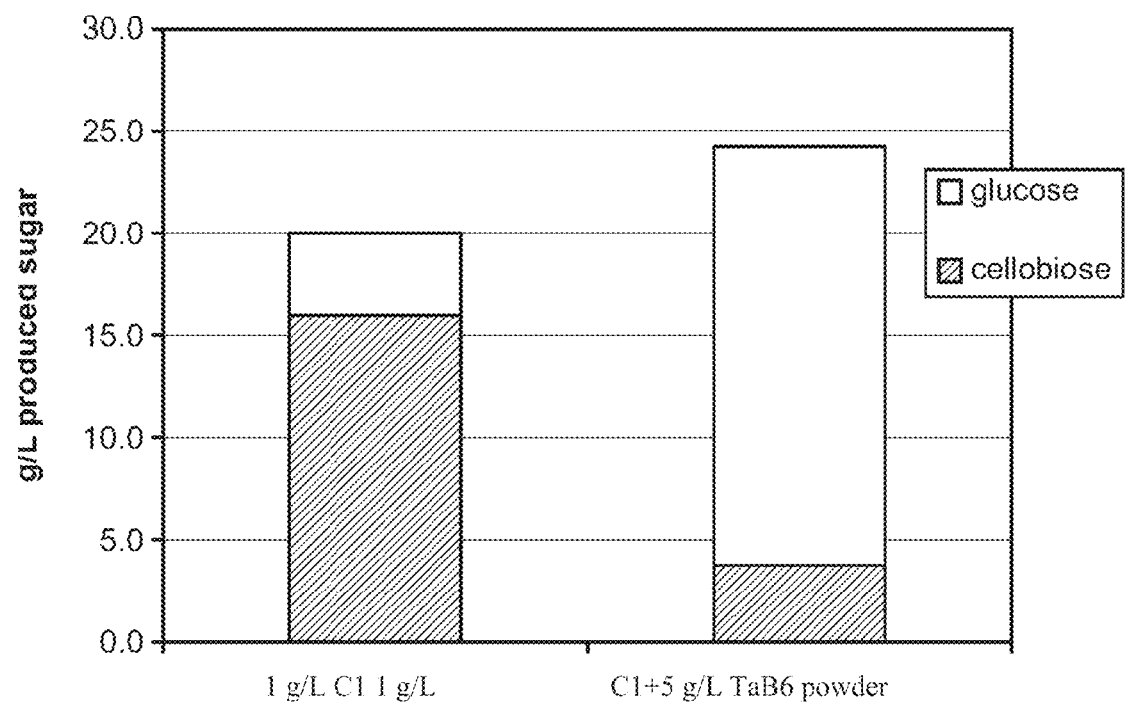

SEQUENCE LISTING

<160> NUMBER OF SEQ ID NOS: 7

<210> SEQ ID NO 1
<211> LENGTH: 2526
<212> TYPE: DNA
<213> ORGANISM: Thermoascus aurantiacus

<400> SEQUENCE: 1

```
aaggatgact tggcctactc gccgccttc taccegtcgc cgtggatgga cggaaacgga      60
gagtgggcgg aggcctaccg cagggctgtc gacttcgtct cgcagctgac cctcgcggag    120
aaggtcaacc tgacgaccgg tgtcgggtgg atgcaggaga aatgtgtcgg tgaaacgggc    180
agcattccga ggctggggtt ccgtggactg tgcctccaag actcgcccct tggtgtcaga    240
tttgctgact acgtttctgc cttccccgcc ggtgtcaacg tcgctgcaac gtgggataag    300
aacctcgcct accttcgtgg gaaggcgatg ggtgaggaac accgtggtaa gggcgtcgac    360
gtccagctgg gacctgtcgc cggccctctt ggcagacacc ccgacggtgg cagaaactgg    420
gagggtttct ctcctgaccc cgtcctgacc ggtgtgctta tggcggagac gatcaagggt    480
atccaggacg ccggtgtgat tgcttgcgcc aagcacttca ttggtaacga gatggagcac    540
ttccggcaag ccagtgaggc tgttggttat ggtttcgata ttaccgagag tgtcagctca    600
aatatcgacg acaagacgct tcacgagctg tacctttggc cctttgcgga tgctgttcgc    660
gctggcgttg gttcgttcat gtgctcctac aaccaggtta caacagcta cagctgctcg    720 aacagctacc tcctaaacaa gttgctcaaa tcggagcttg attttcaggg cttcgtgatg    780
agtgactggg gagcgcacca cagcggcgtt ggagctgccc tggctggcct tgacatgtcg    840
atgccaggag acaccgcctt tggtaccggc aaatccttct ggggaaccaa cctgaccatc    900
gccgttctca acggcactgt tccggaatgg cgtgtggatg acatggctgt tcgcatcatg    960 gcggccttt acaaggttgg tcgcgaccgt taccaggtgc cggtcaactt cgactcgtgg   1020
acgaaggatg aatacggtta cgagcacgca ctggttggcc agaactatgt caaggtcaat   1080
gacaaggtgg atgttcgtgc cgaccatgcg gacatcatcc gtcaaattgg gtctgctagt   1140
gttgtccttc ttaagaacga tggaggactc ccattgaccg gctatgaaaa gttcaccgga   1200 gttttggag aggatgccgg atcgaaccgt tggggcgctg acggctgctc tgatcgtggt   1260
tgcgacaacg gcacgttggc aatgggttgg ggcagtggca ctgctgactt cccctacctt   1320
```

```
gtcactcccg agcaggcaat ccagaatgaa atcctttcca aggggaaggg gttagtgagt    1380
gctgtcaccg acaatggtgc cctggaccag atggaacagg ttgcgtctca ggccagcgtt    1440
tctatcgttt tcgtcaacgc cgactctggt gaaggctaca tcaacgttga tggcaacgaa    1500
ggtgatcgga agaacctcac cctctggaag ggaggcgagg aggtgatcaa gactgttgca    1560
gccaactgca acaacaccat tgttgtgatg cacactgtgg acctgtcttg atcgatgag     1620 tggtatgaca accccaacgt caccgccatc gtctgggccg tcttccaggc caggagagc     1680 ggcaacagtc tcgtcgatgt gctctacggc cgtgtcagcc ccggaggaaa gacgccgttt    1740
acgtggggaa agactcgcga gtcgtacggc gctcctctgc tcaccaaacc caacaacggc    1800
aagggtgccc cccaggacga cttcaccgag ggcgtcttca tcgactacag aaggttcgac    1860
aagtacaacg agacgcccat ctatgagttc gggtttggtc tgagttatac cacttttgaa    1920
tactcggaca tctacgtcca gccccttaac gcacgacctt acaccccagc ctccggcagc    1980
accaaggcgg ctcctacctt tgggaacatc agcacggact atgcagatta cttgtacccct   2040 gaggatatac acaaggtccc attatacatc tatccttggc ttaacacgac ggacccgaag    2100
aagtcctccg cgatcccga ctacggaatg aaggccgagg actacatccc atctggcgcg     2160
actgatggat ctcctcagcc catccttccg gcaggcggtg ctcctggtgg caacccgggt    2220
ctctatgatg agatgtacag ggtatctgca atcatcacca acaccggtaa cgttgttggt    2280
gatgaggttc ctcagctgta tgtctctctt ggtggtccag atgaccccaa ggtcgtgctc    2340
cgcaactttg accgcatcac gctccacccc ggccagcaga caatgtggac cacgacattg    2400
acgcgacgcg atatctcgaa ctgggaccct gcctcccaga attgggttgt gaccaaatat    2460
cccaagacag tctacatcgg cagctcttcg cggaaactgc acctgcaggc accgcttccc    2520
ccttac                                                                2526

<210> SEQ ID NO 2
<211> LENGTH: 842
<212> TYPE: PRT
<213> ORGANISM: Thermoascus aurantiacus

<400> SEQUENCE: 2

Lys Asp Asp Leu Ala Tyr Ser Pro Pro Phe Tyr Pro Ser Pro Trp Met
1               5                   10                  15

Asp Gly Asn Gly Glu Trp Ala Glu Ala Tyr Arg Arg Ala Val Asp Phe
            20                  25                  30

Val Ser Gln Leu Thr Leu Ala Glu Lys Val Asn Leu Thr Thr Gly Val
        35                  40                  45

Gly Trp Met Gln Glu Lys Cys Val Gly Glu Thr Gly Ser Ile Pro Arg
    50                  55                  60

Leu Gly Phe Arg Gly Leu Cys Leu Gln Asp Ser Pro Leu Gly Val Arg
65                  70                  75                  80

Phe Ala Asp Tyr Val Ser Ala Phe Pro Ala Gly Val Asn Val Ala Ala
                85                  90                  95

Thr Trp Asp Lys Asn Leu Ala Tyr Leu Arg Gly Lys Ala Met Gly Glu
            100                 105                 110

Glu His Arg Gly Lys Gly Val Asp Val Gln Leu Gly Pro Val Ala Gly
        115                 120                 125

Pro Leu Gly Arg His Pro Asp Gly Gly Arg Asn Trp Glu Gly Phe Ser
    130                 135                 140

Pro Asp Pro Val Leu Thr Gly Val Leu Met Ala Glu Thr Ile Lys Gly
145                 150                 155                 160
```

```
Ile Gln Asp Ala Gly Val Ile Ala Cys Ala Lys His Phe Ile Gly Asn
                165                 170                 175
Glu Met Glu His Phe Arg Gln Ala Ser Glu Ala Val Gly Tyr Gly Phe
            180                 185                 190
Asp Ile Thr Glu Ser Val Ser Ser Asn Ile Asp Asp Lys Thr Leu His
        195                 200                 205
Glu Leu Tyr Leu Trp Pro Phe Ala Asp Ala Val Arg Ala Gly Val Gly
    210                 215                 220
Ser Phe Met Cys Ser Tyr Asn Gln Val Asn Asn Ser Tyr Ser Cys Ser
225                 230                 235                 240
Asn Ser Tyr Leu Leu Asn Lys Leu Leu Lys Ser Glu Leu Asp Phe Gln
                245                 250                 255
Gly Phe Val Met Ser Asp Trp Gly Ala His His Ser Gly Val Gly Ala
            260                 265                 270
Ala Leu Ala Gly Leu Asp Met Ser Met Pro Gly Asp Thr Ala Phe Gly
        275                 280                 285
Thr Gly Lys Ser Phe Trp Gly Thr Asn Leu Thr Ile Ala Val Leu Asn
    290                 295                 300
Gly Thr Val Pro Glu Trp Arg Val Asp Asp Met Ala Val Arg Ile Met
305                 310                 315                 320
Ala Ala Phe Tyr Lys Val Gly Arg Asp Arg Tyr Gln Val Pro Val Asn
                325                 330                 335
Phe Asp Ser Trp Thr Lys Asp Glu Tyr Gly Tyr Glu His Ala Leu Val
            340                 345                 350
Gly Gln Asn Tyr Val Lys Val Asn Asp Lys Val Asp Val Arg Ala Asp
        355                 360                 365
His Ala Asp Ile Ile Arg Gln Ile Gly Ser Ala Ser Val Val Leu Leu
    370                 375                 380
Lys Asn Asp Gly Gly Leu Pro Leu Thr Gly Tyr Glu Lys Phe Thr Gly
385                 390                 395                 400
Val Phe Gly Glu Asp Ala Gly Ser Asn Arg Trp Gly Ala Asp Gly Cys
                405                 410                 415
Ser Asp Arg Gly Cys Asp Asn Gly Thr Leu Ala Met Gly Trp Gly Ser
            420                 425                 430
Gly Thr Ala Asp Phe Pro Tyr Leu Val Thr Pro Glu Gln Ala Ile Gln
        435                 440                 445
Asn Glu Ile Leu Ser Lys Gly Lys Gly Leu Val Ser Ala Val Thr Asp
    450                 455                 460
Asn Gly Ala Leu Asp Gln Met Glu Gln Val Ala Ser Gln Ala Ser Val
465                 470                 475                 480
Ser Ile Val Phe Val Asn Ala Asp Ser Gly Glu Gly Tyr Ile Asn Val
                485                 490                 495
Asp Gly Asn Glu Gly Asp Arg Lys Asn Leu Thr Leu Trp Lys Gly Gly
            500                 505                 510
Glu Glu Val Ile Lys Thr Val Ala Ala Asn Cys Asn Asn Thr Ile Val
        515                 520                 525
Val Met His Thr Val Gly Pro Val Leu Ile Asp Glu Trp Tyr Asp Asn
    530                 535                 540
Pro Asn Val Thr Ala Ile Val Trp Ala Gly Leu Pro Gly Gln Glu Ser
545                 550                 555                 560
Gly Asn Ser Leu Val Asp Val Leu Tyr Gly Arg Val Ser Pro Gly Gly
                565                 570                 575
Lys Thr Pro Phe Thr Trp Gly Lys Thr Arg Glu Ser Tyr Gly Ala Pro
```

```
                           580                 585                 590
Leu Leu Thr Lys Pro Asn Asn Gly Lys Gly Ala Pro Gln Asp Asp Phe
                595                 600                 605

Thr Glu Gly Val Phe Ile Asp Tyr Arg Arg Phe Asp Lys Tyr Asn Glu
            610                 615                 620

Thr Pro Ile Tyr Glu Phe Gly Phe Gly Leu Ser Tyr Thr Thr Phe Glu
625                 630                 635                 640

Tyr Ser Asp Ile Tyr Val Gln Pro Leu Asn Ala Arg Pro Tyr Thr Pro
                645                 650                 655

Ala Ser Gly Ser Thr Lys Ala Ala Pro Thr Phe Gly Asn Ile Ser Thr
            660                 665                 670

Asp Tyr Ala Asp Tyr Leu Tyr Pro Glu Asp Ile His Lys Val Pro Leu
        675                 680                 685

Tyr Ile Tyr Pro Trp Leu Asn Thr Thr Asp Pro Lys Lys Ser Ser Gly
        690                 695                 700

Asp Pro Asp Tyr Gly Met Lys Ala Glu Asp Tyr Ile Pro Ser Gly Ala
705                 710                 715                 720

Thr Asp Gly Ser Pro Gln Pro Ile Leu Pro Ala Gly Ala Pro Gly
                725                 730                 735

Gly Asn Pro Gly Leu Tyr Asp Glu Met Tyr Arg Val Ser Ala Ile Ile
            740                 745                 750

Thr Asn Thr Gly Asn Val Val Gly Asp Glu Val Pro Gln Leu Tyr Val
        755                 760                 765

Ser Leu Gly Gly Pro Asp Asp Pro Lys Val Val Leu Arg Asn Phe Asp
        770                 775                 780

Arg Ile Thr Leu His Pro Gly Gln Gln Thr Met Trp Thr Thr Thr Leu
785                 790                 795                 800

Thr Arg Arg Asp Ile Ser Asn Trp Asp Pro Ala Ser Gln Asn Trp Val
                805                 810                 815

Val Thr Lys Tyr Pro Lys Thr Val Tyr Ile Gly Ser Ser Arg Lys
            820                 825                 830

Leu His Leu Gln Ala Pro Leu Pro Pro Tyr
        835                 840

<210> SEQ ID NO 3
<211> LENGTH: 2529
<212> TYPE: DNA
<213> ORGANISM: Artificial
<220> FEATURE:
<223> OTHER INFORMATION: Synthetic DNA construct

<400> SEQUENCE: 3
atgaaggatg acttggccta ctcgccgcct ttctacccgt cgccgtggat ggacggaaac      60
ggagagtggg cggaggccta ccgcagggct gtcgacttcg tctcgcagct gaccctcgcg     120
gagaaggtca acctgacgac cggtgtcggg tggatgcagg agaaatgtgt cggtgaaacg     180
ggcagcattc cgaggctggg gttccgtgga ctgtgcctcc aagactcgcc ccttggtgtc     240
agatttgctg actacgtttc tgccttcccc gccggtgtca acgtcgctgc aacgtgggat     300
aagaacctcg cctaccttcg tgggaaggcg atgggtgagg aacaccgtgg taagggcgtc     360
gacgtccagc tggacctgt cgccggccct cttggcagac accccgacgg tgcagaaac     420 tgggagggtt tctctcctga ccccgtcctg accggtgtgc ttatggcgga gacgatcaag     480
ggtatccagg acgccggtgt gattgcttgc gccaagcact cattggtaa cgagatggag     540 cacttccggc aagccagtga ggctgttggt tatggtttcg atattaccga gagtgtcagc     600
```

```
tcaaatatcg acgacaagac gcttcacgag ctgtaccttt ggcccttttgc ggatgctgtt    660
cgcgctggcg ttggttcgtt catgtgctcc tacaaccagg ttaacaacag ctacagctgc    720
tcgaacagct acctcctaaa caagttgctc aaatcggagc ttgattttca gggcttcgtg    780
atgagtgact ggggagcgca ccacagcggc gttggagctg ccctggctgg ccttgacatg    840
tcgatgccag agacaccgc ctttggtacc ggcaaatcct tctggggaac caacctgacc    900
atcgccgttc tcaacggcac tgttccggaa tggcgtgtgg atgacatggc tgttcgcatc    960
atggcggcct tttacaaggt tggtcgcgac cgttaccagg tgccggtcaa cttcgactcg   1020
tggacgaagg atgaatacgg ttacgagcac gcactggttg ccagaactca tgtcaaggtc   1080
aatgacaagg tggatgttcg tgccgaccat gcggacatca tccgtcaaat tgggtctgct   1140
agtgttgtcc ttcttaagaa cgatggagga ctcccattga ccggctatga aaagttcacc   1200
ggagttttg gagaggatgc cggatcgaac cgttggggcg ctgacggctg ctctgatcgt   1260
ggttgcgaca acggcacgtt ggcaatgggt tgggcagtg gcactgctga cttcccctac   1320
cttgtcactc ccgagcaggc aatccagaat gaaatccttt ccaaggggaa ggggttagtg   1380
agtgctgtca ccgacaatgg tgccctggac agatggaaac aggttgcgtc tcaggccagc   1440
gtttctatcg ttttcgtcaa cgccgactct ggtgaaggct acatcaacgt tgatggcaac   1500
gaaggtgatc ggaagaacct caccctctgg aagggaggcg aggaggtgat caagactgtt   1560
gcagccaact gcaacaacac cattgttgtg atgcacactg tgggacctgt cttgatcgat   1620
gagtggtatg acaaccccaa cgtcaccgcc atcgtctggg ccggtcttcc aggccaggag   1680
agcggcaaca gtctcgtcga tgtgctctac ggccgtgtca gccccggagg aaagacgccg   1740
tttacgtggg gaaagactcg cgagtcgtac ggcgctcctc tgctcaccaa acccaacaac   1800
ggcaagggtg cccccagga cgacttcacc gagggcgtct tcatcgacta cagaaggttc   1860
gacaagtaca acgagacgcc catctatgag ttcgggtttg gtctgagtta taccactttt   1920
gaatactcgg acatctacgt ccagccccctt aacgcacgac cttacacccc agcctccggc   1980
agcaccaagg cggctcctac ctttgggaac atcagcacgg actatgcaga ttacttgtac   2040
cctgaggata tacacaaggt cccattatac atctatcctt ggcttaacac gacggacccg   2100
aagaagtcct ccggcgatcc cgactacgga atgaaggccg aggactacat cccatctggc   2160
gcgactgatg gatctcctca gcccatcctt ccggcaggcg gtgctcctgg tggcaacccg   2220
ggtctctatg atgagatgta cagggtatct gcaatcatca ccaacaccgg taacgttgtt   2280
ggtgatgagg ttcctcagct gtatgtctct cttggtggtc cagatgaccc caaggtcgtg   2340
ctccgcaact tgaccgcat cacgctccac cccggccagc agacaatgtg gaccacgaca   2400
ttgacgcgac gcgatatctc gaactgggac cctgcctccc agaattgggt tgtgaccaaa   2460
tatcccaaga cagtctacat cggcagctct tcgcggaaac tgcacctgca ggcaccgctt   2520
cccccttac                                                          2529
```

<210> SEQ ID NO 4
<211> LENGTH: 843
<212> TYPE: PRT
<213> ORGANISM: Artificial
<220> FEATURE:
<223> OTHER INFORMATION: Synthetic polypeptide

<400> SEQUENCE: 4

Met Lys Asp Asp Leu Ala Tyr Ser Pro Pro Phe Tyr Pro Ser Pro Trp
1               5                   10                  15

Met Asp Gly Asn Gly Glu Trp Ala Glu Ala Tyr Arg Arg Ala Val Asp

-continued

```
                20                  25                  30
Phe Val Ser Gln Leu Thr Leu Ala Glu Lys Val Asn Leu Thr Thr Gly
            35                  40                  45
Val Gly Trp Met Gln Glu Lys Cys Val Gly Glu Thr Gly Ser Ile Pro
        50                  55                  60
Arg Leu Gly Phe Arg Gly Leu Cys Leu Gln Asp Ser Pro Leu Gly Val
65                  70                  75                  80
Arg Phe Ala Asp Tyr Val Ser Ala Phe Pro Ala Gly Val Asn Val Ala
                85                  90                  95
Ala Thr Trp Asp Lys Asn Leu Ala Tyr Leu Arg Gly Lys Ala Met Gly
            100                 105                 110
Glu Glu His Arg Gly Lys Gly Val Asp Val Gln Leu Gly Pro Val Ala
        115                 120                 125
Gly Pro Leu Gly Arg His Pro Asp Gly Gly Arg Asn Trp Glu Gly Phe
130                 135                 140
Ser Pro Asp Pro Val Leu Thr Gly Val Leu Met Ala Glu Thr Ile Lys
145                 150                 155                 160
Gly Ile Gln Asp Ala Gly Val Ile Ala Cys Ala Lys His Phe Ile Gly
                165                 170                 175
Asn Glu Met Glu His Phe Arg Gln Ala Ser Glu Ala Val Gly Tyr Gly
            180                 185                 190
Phe Asp Ile Thr Glu Ser Val Ser Ser Asn Ile Asp Asp Lys Thr Leu
        195                 200                 205
His Glu Leu Tyr Leu Trp Pro Phe Ala Asp Ala Val Arg Ala Gly Val
210                 215                 220
Gly Ser Phe Met Cys Ser Tyr Asn Gln Val Asn Asn Ser Tyr Ser Cys
225                 230                 235                 240
Ser Asn Ser Tyr Leu Leu Asn Lys Leu Leu Lys Ser Glu Leu Asp Phe
                245                 250                 255
Gln Gly Phe Val Met Ser Asp Trp Gly Ala His His Ser Gly Val Gly
            260                 265                 270
Ala Ala Leu Ala Gly Leu Asp Met Ser Met Pro Gly Asp Thr Ala Phe
        275                 280                 285
Gly Thr Gly Lys Ser Phe Trp Gly Thr Asn Leu Thr Ile Ala Val Leu
290                 295                 300
Asn Gly Thr Val Pro Glu Trp Arg Val Asp Asp Met Ala Val Arg Ile
305                 310                 315                 320
Met Ala Ala Phe Tyr Lys Val Gly Arg Asp Arg Tyr Gln Val Pro Val
                325                 330                 335
Asn Phe Asp Ser Trp Thr Lys Asp Glu Tyr Gly Tyr Glu His Ala Leu
            340                 345                 350
Val Gly Gln Asn Tyr Val Lys Val Asn Asp Lys Val Asp Val Arg Ala
        355                 360                 365
Asp His Ala Asp Ile Ile Arg Gln Ile Gly Ser Ala Ser Val Val Leu
370                 375                 380
Leu Lys Asn Asp Gly Gly Leu Pro Leu Thr Gly Tyr Glu Lys Phe Thr
385                 390                 395                 400
Gly Val Phe Gly Glu Asp Ala Gly Ser Asn Arg Trp Gly Ala Asp Gly
                405                 410                 415
Cys Ser Asp Arg Gly Cys Asp Asn Gly Thr Leu Ala Met Gly Trp Gly
            420                 425                 430
Ser Gly Thr Ala Asp Phe Pro Tyr Leu Val Thr Pro Glu Gln Ala Ile
        435                 440                 445
```

Gln Asn Glu Ile Leu Ser Lys Gly Lys Gly Leu Val Ser Ala Val Thr
450                 455                 460

Asp Asn Gly Ala Leu Asp Gln Met Glu Gln Val Ala Ser Gln Ala Ser
465                 470                 475                 480

Val Ser Ile Val Phe Val Asn Ala Asp Ser Gly Glu Gly Tyr Ile Asn
                485                 490                 495

Val Asp Gly Asn Glu Gly Asp Arg Lys Asn Leu Thr Leu Trp Lys Gly
                500                 505                 510

Gly Glu Glu Val Ile Lys Thr Val Ala Ala Asn Cys Asn Asn Thr Ile
                515                 520                 525

Val Val Met His Thr Val Gly Pro Val Leu Ile Asp Glu Trp Tyr Asp
530                 535                 540

Asn Pro Asn Val Thr Ala Ile Val Trp Ala Gly Leu Pro Gly Gln Glu
545                 550                 555                 560

Ser Gly Asn Ser Leu Val Asp Val Leu Tyr Gly Arg Val Ser Pro Gly
                565                 570                 575

Gly Lys Thr Pro Phe Thr Trp Gly Lys Thr Arg Glu Ser Tyr Gly Ala
                580                 585                 590

Pro Leu Leu Thr Lys Pro Asn Asn Gly Lys Gly Ala Pro Gln Asp Asp
                595                 600                 605

Phe Thr Glu Gly Val Phe Ile Asp Tyr Arg Arg Phe Asp Lys Tyr Asn
610                 615                 620

Glu Thr Pro Ile Tyr Glu Phe Gly Phe Gly Leu Ser Tyr Thr Thr Phe
625                 630                 635                 640

Glu Tyr Ser Asp Ile Tyr Val Gln Pro Leu Asn Ala Arg Pro Tyr Thr
                645                 650                 655

Pro Ala Ser Gly Ser Thr Lys Ala Ala Pro Thr Phe Gly Asn Ile Ser
                660                 665                 670

Thr Asp Tyr Ala Asp Tyr Leu Tyr Pro Glu Asp Ile His Lys Val Pro
                675                 680                 685

Leu Tyr Ile Tyr Pro Trp Leu Asn Thr Thr Asp Pro Lys Lys Ser Ser
690                 695                 700

Gly Asp Pro Asp Tyr Gly Met Lys Ala Glu Asp Tyr Ile Pro Ser Gly
705                 710                 715                 720

Ala Thr Asp Gly Ser Pro Gln Pro Ile Leu Pro Ala Gly Gly Ala Pro
                725                 730                 735

Gly Gly Asn Pro Gly Leu Tyr Asp Glu Met Tyr Arg Val Ser Ala Ile
                740                 745                 750

Ile Thr Asn Thr Gly Asn Val Val Gly Asp Glu Val Pro Gln Leu Tyr
                755                 760                 765

Val Ser Leu Gly Gly Pro Asp Asp Pro Lys Val Val Leu Arg Asn Phe
770                 775                 780

Asp Arg Ile Thr Leu His Pro Gly Gln Gln Thr Met Trp Thr Thr Thr
785                 790                 795                 800

Leu Thr Arg Arg Asp Ile Ser Asn Trp Asp Pro Ala Ser Gln Asn Trp
                805                 810                 815

Val Val Thr Lys Tyr Pro Lys Thr Val Tyr Ile Gly Ser Ser Ser Arg
                820                 825                 830

Lys Leu His Leu Gln Ala Pro Leu Pro Pro Tyr
            835                 840

<210> SEQ ID NO 5
<211> LENGTH: 2583
<212> TYPE: DNA
<213> ORGANISM: Thermoascus aurantiacus -continued

<400> SEQUENCE: 5

```
atgaggcttg ggtggctgga gctggccgtc gcggcggccg cgaccgtcgc cagcgccaag    60
gatgacttgg cctactcgcc gcctttctac ccgtcgccgt ggatggacgg aaacggagag   120
tgggcggagg cctaccgcag ggctgtcgac ttcgtctcgc agctgaccct cgcggagaag   180
gtcaacctga cgaccggtgt cgggtggatg caggagaaat gtgtcggtga acgggcagc    240
attccgaggc tggggttccg tggactgtgc ctccaagact cgccccttgg tgtcagattt   300
gctgactacg tttctgcctt ccccgccggt gtcaacgtcg ctgcaacgtg gataagaac    360
ctcgcctacc ttcgtgggaa ggcgatgggt gaggaacacc gtggtaaggg cgtcgacgtc   420
cagctgggac ctgtcgccgg ccctcttggc agacaccccg acggtggcag aaactgggag   480
ggtttctctc ctgaccccgt cctgaccggt gtgcttatgg cggagacgat caagggtatc   540
caggacgccg tgtgattgc ttgcgccaag cacttcattg taacgagat ggagcacttc     600
cggcaagcca gtgaggctgt tggttatggt ttcgatatta ccgagagtgt cagctcaaat   660
atcgacgaca agacgcttca cgagctgtac ctttggcccct tgcggatgc tgttcgcgct   720
ggcgttggtt cgttcatgtg ctcctacaac caggttaaca acagctacag ctgctcgaac   780
agctacctcc taaacaagtt gctcaaatcg agcttgatt ttcagggctt cgtgatgagt    840
gactggggag cgcaccacag cggcgttgga gctgccctgg ctggccttga catgtcgatg   900
ccaggagaca ccgcctttgg taccggcaaa tccttctggg gaaccaacct gaccatcgcc   960
gttctcaacg gcactgttcc ggaatggcgt gtggatgaca tggctgttcg catcatggcg  1020
gcctttaca aggttggtcg cgaccgttac caggtgccgg tcaacttcga ctcgtggacg   1080
aaggatgaat acgttacga gcacgcactg gttggccaga actatgtcaa ggtcaatgac   1140
aaggtggatg ttcgtgccga ccatgcggac atcatccgtc aaattgggtc tgctagtgtt  1200
gtccttctta agaacgatgg aggactccca ttgaccggct atgaaaagtt caccggagtt   1260
tttggagagg atgccggatc gaaccgttgg ggcgctgacg gctgctctga tcgtggttgc  1320
gacaacggca cgttggcaat gggttggggc agtggcactg ctgacttccc ctaccttgtc  1380
actcccgagc aggcaatcca gaatgaaatc cttttccaagg ggaaggggtt agtgagtgct  1440
gtcaccgaca atggtgccct ggaccagatg aacaggttg cgtctcaggc cagcgttttct  1500
atcgttttcg tcaacgccga ctctggtgaa ggctacatca acgttgatgg caacgaaggt  1560
gatcggaaga acctcacccct ctggaaggga ggcgaggagg tgatcaagac tgttgcagcc  1620
aactgcaaca acaccattgt tgtgatgcac actgtgggac ctgtcttgat cgatgagtgg  1680
tatgacaacc ccaacgtcac cgccatcgtc tgggccggtc ttccaggcca ggagagcggc  1740
aacagtctcg tcgatgtgct ctacggccgt gtcagccccg aggaaagac gccgtttacg   1800
tgggaaaga ctcgcgagtc gtacggcgct cctctgctca ccaaacccaa caacggcaag  1860
ggtgccccc aggacgactt caccgagggc gtcttcatcg actacagaag gttcgacaag  1920
tacaacgaga cgcccatcta tgagttcggg tttggtctga ttataccac ttttgaatac  1980
tcggacatct acgtccagcc ccttaacgca cgaccttaca ccccagcctc cggcagcacc  2040
aaggcggctc ctacctttgg gaacatcagc acggactatg cagattactt gtaccctgag  2100
gatatacaca aggtcccatt atacatctat ccttggctta acacgacgga cccgaagaag  2160
tcctccggcg atccgactta cggaatgaag gccgaggact acatcccatc tggcgcgact  2220
gatgatctc ctcagcccat ccttccggca ggcggtgctc ctggtggcaa cccgggtctc  2280
tatgatgaga tgtacagggt atctgcaatc atcaccaaca ccggtaacgt tgttggtgat  2340
```

-continued

```
gaggttcctc agctgtatgt ctctcttggt ggtccagatg accccaaggt cgtgctccgc    2400
aactttgacc gcatcacgct ccaccccggc cagcagacaa tgtggaccac gacattgacg    2460
cgacgcgata tctcgaactg ggaccctgcc tcccagaatt gggttgtgac caaatatccc    2520
aagacagtct acatcggcag ctcttcgcgg aaactgcacc tgcaggcacc gcttcccct    2580 tac                                                                  2583
```

```
<210> SEQ ID NO 6
<211> LENGTH: 861
<212> TYPE: PRT
<213> ORGANISM: Thermoascus aurantiacus

<400> SEQUENCE: 6
```

| Met | Arg | Leu | Gly | Trp | Leu | Glu | Leu | Ala | Val | Ala | Ala | Ala | Thr | Val |
|---|---|---|---|---|---|---|---|---|---|---|---|---|---|---|
| 1 | | | | 5 | | | | | 10 | | | | | 15 |

| Ala | Ser | Ala | Lys | Asp | Asp | Leu | Ala | Tyr | Ser | Pro | Pro | Phe | Tyr | Pro | Ser |
|---|---|---|---|---|---|---|---|---|---|---|---|---|---|---|---|
| | | | 20 | | | | | 25 | | | | | 30 | | |

| Pro | Trp | Met | Asp | Gly | Asn | Gly | Glu | Trp | Ala | Glu | Ala | Tyr | Arg | Arg | Ala |
|---|---|---|---|---|---|---|---|---|---|---|---|---|---|---|---|
| | | 35 | | | | 40 | | | | | 45 | | | | |

| Val | Asp | Phe | Val | Ser | Gln | Leu | Thr | Leu | Ala | Glu | Lys | Val | Asn | Leu | Thr |
|---|---|---|---|---|---|---|---|---|---|---|---|---|---|---|---|
| | 50 | | | | | 55 | | | | | 60 | | | | |

| Thr | Gly | Val | Gly | Trp | Met | Gln | Glu | Lys | Cys | Val | Gly | Glu | Thr | Gly | Ser |
|---|---|---|---|---|---|---|---|---|---|---|---|---|---|---|---|
| 65 | | | | | 70 | | | | | 75 | | | | | 80 |

| Ile | Pro | Arg | Leu | Gly | Phe | Arg | Gly | Leu | Cys | Leu | Gln | Asp | Ser | Pro | Leu |
|---|---|---|---|---|---|---|---|---|---|---|---|---|---|---|---|
| | | | | 85 | | | | | 90 | | | | | 95 | |

| Gly | Val | Arg | Phe | Ala | Asp | Tyr | Val | Ser | Ala | Phe | Pro | Ala | Gly | Val | Asn |
|---|---|---|---|---|---|---|---|---|---|---|---|---|---|---|---|
| | | | 100 | | | | | 105 | | | | | 110 | | |

| Val | Ala | Ala | Thr | Trp | Asp | Lys | Asn | Leu | Ala | Tyr | Leu | Arg | Gly | Lys | Ala |
|---|---|---|---|---|---|---|---|---|---|---|---|---|---|---|---|
| | | 115 | | | | 120 | | | | | 125 | | | | |

| Met | Gly | Glu | Glu | His | Arg | Gly | Lys | Gly | Val | Asp | Val | Gln | Leu | Gly | Pro |
|---|---|---|---|---|---|---|---|---|---|---|---|---|---|---|---|
| | 130 | | | | | 135 | | | | | 140 | | | | |

| Val | Ala | Gly | Pro | Leu | Gly | Arg | His | Pro | Asp | Gly | Gly | Arg | Asn | Trp | Glu |
|---|---|---|---|---|---|---|---|---|---|---|---|---|---|---|---|
| 145 | | | | | 150 | | | | | 155 | | | | | 160 |

| Gly | Phe | Ser | Pro | Asp | Pro | Val | Leu | Thr | Gly | Val | Leu | Met | Ala | Glu | Thr |
|---|---|---|---|---|---|---|---|---|---|---|---|---|---|---|---|
| | | | | 165 | | | | | 170 | | | | | 175 | |

| Ile | Lys | Gly | Ile | Gln | Asp | Ala | Gly | Val | Ile | Ala | Cys | Ala | Lys | His | Phe |
|---|---|---|---|---|---|---|---|---|---|---|---|---|---|---|---|
| | | | 180 | | | | | 185 | | | | | 190 | | |

| Ile | Gly | Asn | Glu | Met | Glu | His | Phe | Arg | Gln | Ala | Ser | Glu | Ala | Val | Gly |
|---|---|---|---|---|---|---|---|---|---|---|---|---|---|---|---|
| | | 195 | | | | 200 | | | | | 205 | | | | |

| Tyr | Gly | Phe | Asp | Ile | Thr | Glu | Ser | Val | Ser | Ser | Asn | Ile | Asp | Asp | Lys |
|---|---|---|---|---|---|---|---|---|---|---|---|---|---|---|---|
| | 210 | | | | | 215 | | | | | 220 | | | | |

| Thr | Leu | His | Glu | Leu | Tyr | Leu | Trp | Pro | Phe | Ala | Asp | Ala | Val | Arg | Ala |
|---|---|---|---|---|---|---|---|---|---|---|---|---|---|---|---|
| 225 | | | | | 230 | | | | | 235 | | | | | 240 |

| Gly | Val | Gly | Ser | Phe | Met | Cys | Ser | Tyr | Asn | Gln | Val | Asn | Asn | Ser | Tyr |
|---|---|---|---|---|---|---|---|---|---|---|---|---|---|---|---|
| | | | | 245 | | | | | 250 | | | | | 255 | |

| Ser | Cys | Ser | Asn | Ser | Tyr | Leu | Leu | Asn | Lys | Leu | Leu | Lys | Ser | Glu | Leu |
|---|---|---|---|---|---|---|---|---|---|---|---|---|---|---|---|
| | | | 260 | | | | | 265 | | | | | 270 | | |

| Asp | Phe | Gln | Gly | Phe | Val | Met | Ser | Asp | Trp | Gly | Ala | His | His | Ser | Gly |
|---|---|---|---|---|---|---|---|---|---|---|---|---|---|---|---|
| | | 275 | | | | 280 | | | | | 285 | | | | |

| Val | Gly | Ala | Ala | Leu | Ala | Gly | Leu | Asp | Met | Ser | Met | Pro | Gly | Asp | Thr |
|---|---|---|---|---|---|---|---|---|---|---|---|---|---|---|---|
| | 290 | | | | | 295 | | | | | 300 | | | | |

| Ala | Phe | Gly | Thr | Gly | Lys | Ser | Phe | Trp | Gly | Thr | Asn | Leu | Thr | Ile | Ala |
|---|---|---|---|---|---|---|---|---|---|---|---|---|---|---|---|
| 305 | | | | | 310 | | | | | 315 | | | | | 320 |

| Val | Leu | Asn | Gly | Thr | Val | Pro | Glu | Trp | Arg | Val | Asp | Asp | Met | Ala | Val |
|---|---|---|---|---|---|---|---|---|---|---|---|---|---|---|---|

-continued

```
                325                 330                 335
Arg Ile Met Ala Ala Phe Tyr Lys Val Gly Arg Asp Arg Tyr Gln Val
                340                 345                 350
Pro Val Asn Phe Asp Ser Trp Thr Lys Asp Glu Tyr Gly Tyr Glu His
                355                 360                 365
Ala Leu Val Gly Gln Asn Tyr Val Lys Val Asn Asp Lys Val Asp Val
                370                 375                 380
Arg Ala Asp His Ala Asp Ile Ile Arg Gln Ile Gly Ser Ala Ser Val
385                 390                 395                 400
Val Leu Leu Lys Asn Asp Gly Gly Leu Pro Leu Thr Gly Tyr Glu Lys
                405                 410                 415
Phe Thr Gly Val Phe Gly Glu Asp Ala Gly Ser Asn Arg Trp Gly Ala
                420                 425                 430
Asp Gly Cys Ser Asp Arg Gly Cys Asp Asn Gly Thr Leu Ala Met Gly
                435                 440                 445
Trp Gly Ser Gly Thr Ala Asp Phe Pro Tyr Leu Val Thr Pro Glu Gln
                450                 455                 460
Ala Ile Gln Asn Glu Ile Leu Ser Lys Gly Lys Gly Leu Val Ser Ala
465                 470                 475                 480
Val Thr Asp Asn Gly Ala Leu Asp Gln Met Glu Gln Val Ala Ser Gln
                485                 490                 495
Ala Ser Val Ser Ile Val Phe Val Asn Ala Asp Ser Gly Glu Gly Tyr
                500                 505                 510
Ile Asn Val Asp Gly Asn Glu Gly Asp Arg Lys Asn Leu Thr Leu Trp
                515                 520                 525
Lys Gly Gly Glu Glu Val Ile Lys Thr Val Ala Ala Asn Cys Asn Asn
530                 535                 540
Thr Ile Val Val Met His Thr Val Gly Pro Val Leu Ile Asp Glu Trp
545                 550                 555                 560
Tyr Asp Asn Pro Asn Val Thr Ala Ile Val Trp Ala Gly Leu Pro Gly
                565                 570                 575
Gln Glu Ser Gly Asn Ser Leu Val Asp Val Leu Tyr Gly Arg Val Ser
                580                 585                 590
Pro Gly Gly Lys Thr Pro Phe Thr Trp Gly Lys Thr Arg Glu Ser Tyr
                595                 600                 605
Gly Ala Pro Leu Leu Thr Lys Pro Asn Asn Gly Lys Gly Ala Pro Gln
                610                 615                 620
Asp Asp Phe Thr Glu Gly Val Phe Ile Asp Tyr Arg Arg Phe Asp Lys
625                 630                 635                 640
Tyr Asn Glu Thr Pro Ile Tyr Glu Phe Gly Phe Gly Leu Ser Tyr Thr
                645                 650                 655
Thr Phe Glu Tyr Ser Asp Ile Tyr Val Gln Pro Leu Asn Ala Arg Pro
                660                 665                 670
Tyr Thr Pro Ala Ser Gly Ser Thr Lys Ala Ala Pro Thr Phe Gly Asn
                675                 680                 685
Ile Ser Thr Asp Tyr Ala Asp Tyr Leu Tyr Pro Glu Asp Ile His Lys
                690                 695                 700
Val Pro Leu Tyr Ile Tyr Pro Trp Leu Asn Thr Thr Asp Pro Lys Lys
705                 710                 715                 720
Ser Ser Gly Asp Pro Asp Tyr Gly Met Lys Ala Glu Asp Tyr Ile Pro
                725                 730                 735
Ser Gly Ala Thr Asp Gly Ser Pro Gln Pro Ile Leu Pro Ala Gly Gly
                740                 745                 750
```

```
Ala Pro Gly Gly Asn Pro Gly Leu Tyr Asp Glu Met Tyr Arg Val Ser
            755                 760                 765

Ala Ile Ile Thr Asn Thr Gly Asn Val Val Gly Asp Glu Val Pro Gln
        770                 775                 780

Leu Tyr Val Ser Leu Gly Gly Pro Asp Asp Pro Lys Val Val Leu Arg
785                 790                 795                 800

Asn Phe Asp Arg Ile Thr Leu His Pro Gly Gln Gln Thr Met Trp Thr
                805                 810                 815

Thr Thr Leu Thr Arg Arg Asp Ile Ser Asn Trp Asp Pro Ala Ser Gln
            820                 825                 830

Asn Trp Val Val Thr Lys Tyr Pro Lys Thr Val Tyr Ile Gly Ser Ser
        835                 840                 845

Ser Arg Lys Leu His Leu Gln Ala Pro Leu Pro Pro Tyr
    850                 855                 860

<210> SEQ ID NO 7
<211> LENGTH: 2532
<212> TYPE: DNA
<213> ORGANISM: Artificial
<220> FEATURE:
<223> OTHER INFORMATION: Synthetic DNA construct

<400> SEQUENCE: 7
atgaaagatg atttggctta tagtccacct ttctacccat caccttggat ggacggtaac      60
ggagaatggg ctgaagccta tagaagagcc gtcgatttcg tatcccaatt gacattggca     120
gagaaggtaa atttgacaac cggagtgggt tggatgcagg aaaagtgtgt aggcgaaact     180
ggttctatac caagattagg ctttaggggt tgtgcttac aagattctcc cttaggtgta      240
agattcgccg actacgtaag tgcttttcct gcaggagtta acgttgcagc aacttgggat     300
aaaaaccttg catatttgag aggtaaggca atgggtgaag acatcgtgg caagggtgtc      360 gatgtgcagt taggcccagt tgctggacca ttgggaagac atcccgacgg cggaagaaac     420
tgggagggtt ttagtccaga ccccgttttg actggagtct tgatggcaga gactatcaaa     480
ggtatacaag acgctggagt gattgcttgt gctaaacatt tcattggtaa cgaaatggaa     540
catttcagac aagcctccga agcagttggc tatggttttg atattactga gtccgtttca     600
tcaaacatag atgacaaaac ccttcacgaa ctatatttat ggccattcgc tgatgccgtc     660
agagctggtg taggttcttt catgtgttca tacaaccaag tcaacaactc ttattcatgc     720
tctaattcct acttgttgaa caaattatta aagtcagaac ttgactttca aggtttcgta     780
atgtccgact ggggtgctca ccattccgga gttggtgcag cttttggccgg tttagacatg     840 tcaatgccag tgatactgc atttggaacg ggtaaatcct ttggggtac caatctaacc      900 atcgccgtcc ttaatggtac agttcctgaa tggagagtag atgatatggc tgttagaatc     960
atggccgcat tttacaaagt tggtagagat aggtaccaag tgcctgtcaa ctttgactcc    1020
tggaccaaag atgaatatgg ttatgaacac gcattggtgg gccagaatta tgttaaggtc    1080
aatgataaag tggatgtgag agctgaccac gctgatatta ccgtcagat tggtagtgca     1140 tcagttgttt tgttaaaaaa tgacggagga cttcctttaa ctggttatga agttcaca       1200 ggcgtattcg gcgaagatgc cggtagtaat cgttggggtg ctgacggatg cagtgacaga    1260
ggctgcgata tggtaccct tgccatgggt tgggatctg aacggccga ctttccttac       1320 ttagttacgc cagagcaggc tatacaaaat gagattttgt ctaaaggcaa gggacttgtc    1380
tctgccgtga cggataacgg agctttagac caaatggaac aggtcgcttc ccaagcttct    1440
gtaagtattg tttttgttaa tgccgactca ggagaaggct atattaacgt tgatggaaat    1500
```

```
gaaggtgata ggaaaaatct aactctttgg aagggtggtg aagaggtcat taagacagtc    1560
gcagccaatt gtaacaatac catcgtcgta atgcacaccg ttggacctgt gttaatagat    1620
gaatggtatg ataatcctaa tgtcactgca attgtttggg caggcttgcc tggtcaggaa    1680
tccggtaatt ctcttgttga tgtcctatat ggaagggtgt cccctggtgg aaaaactccc    1740
tttacttggg gcaagacacg tgaaagttat ggagcaccat tattaacaaa accaaacaac    1800
ggaaagggag ctcctcaaga tgattttaca gagggtgttt tcatcgacta caggcgtttc    1860
gacaagtata acgagactcc tatatatgag ttcggatttg gtctatccta cacaactttt    1920
gagtactcag atatctacgt acagcccttg aacgcacgtc catacacccc tgcttcaggt    1980
tctactaagg ccgccccaac gtttggaaat atatctactg attacgctga ttacctatac    2040
ccagaggata ttcataaagt tccactttat atctacccat ggcttaatac gacagaccca    2100
aaaaagtcaa gtggtgatcc agattacgga atgaaagctg aagattacat tccttcaggc    2160
gctacggacg gctctcccca accaattcta ccagctggag gtgctccagg tggtaatcct    2220
ggcttgtatg atgagatgta tagggtttct gctataatta caaatacagg taacgttgtt    2280
ggtgatgagg tacctcaact atacgtgtct ttaggtggtc ccgatgaccc caaggtagtt    2340
ttgcgtaact ttgacagaat cactttgcat ccaggacaac aaaccatgtg gactacgact    2400
ttgacaagaa gagatatatc taattgggac cctgcatctc agaattgggt tgtgacaaag    2460
tacccaaaaa ctgtctatat cggctcaagt tccaggaagc ttcacttgca ggcccctcta    2520
cccccatact aa                                                         2532
```

US 8,652,813 B2

RECOMBINANT *THERMOASCUS AURANTIACUS* β-GLUCOSIDASE VARIANTS

The present application claims priority to U.S. Prov. Pat. Appln. Ser. No. 61/264,605, filed Nov. 25, 2009.

FIELD OF THE INVENTION

The present invention provides compositions and methods for the expression of recombinant β-glucosidase variants, as well as their use in the production of fermentable sugars from cellulosic biomass.

BACKGROUND OF THE INVENTION

Cellulosic biomass is a significant renewable resource for the generation of sugars. Fermentation of these sugars can yield commercially valuable end-products, including biofuels and chemicals that are currently derived from petroleum. While the fermentation of simple sugars to ethanol is relatively straightforward, the efficient conversion of cellulosic biomass to fermentable sugars such as glucose is challenging (See e.g., Ladisch et al., Enz. Microb. Technol., 5:82 [1983]). Cellulose may be pretreated chemically, mechanically or in other ways to increase the susceptibility of cellulose to hydrolysis. Such pretreatment may be followed by the enzymatic conversion of cellulose to cellobiose, cello-oligosaccharides, glucose and the like, using enzymes that specialize in breaking down the β-1-4 glycosidic bonds of cellulose. These enzymes are collectively referred to as "cellulases."

Cellulases are divided into three sub-categories of enzymes: 1,4-β-D-glucan glucanohydrolase ("endoglucanase" or "EG"); 1,4-β-D-glucan cellobiohydrolase ("exoglucanase", "cellobiohydrolase", or "CBH"); and β-D-glucoside-glucohydrolase ("β-glucosidase", "cellobiase" or "Bgl"). Endoglucanases randomly attack the interior parts and mainly the amorphous regions of cellulose, mostly yielding glucose, cellotriose, and cellobiose, a water-soluble β-1, 4-linked dimer of glucose. Exoglucanases incrementally shorten the glucan molecules by binding to the glucan ends and releasing mainly cellobiose units from the ends of the cellulose polymer. β-glucosidases split the cellobiose into two units of glucose.

Efficient production of cellulases for use in processing cellulosic biomass would reduce costs and increase the efficiency of production of biofuels and other commercially valuable compounds.

SUMMARY OF THE INVENTION

The present invention provides compositions and methods for the expression of recombinant β-glucosidase variants, as well as their use in the production of fermentable sugars from cellulosic biomass.

In some embodiments, the invention provides an isolated or recombinant *T. aurantiacus* β-glucosidase variant comprising an amino acid sequence that is at least about 70% identical to SEQ ID NO:2 (wild-type *T. aurantiacus* β-glucosidase), or which is encoded by a nucleic acid that hybridizes under stringent conditions to the exact complement of SEQ ID NO:1, and which has at least one substitution relative to SEQ ID NO:2 of an amino acid residue described herein, where the variant has greater enzymatic activity than that of the enzyme set forth in SEQ ID NO:2. In some other embodiments, the present invention provides an isolated β-glucosidase polypeptide variant comprising an amino acid sequence that is at least about 70% identical to SEQ ID NO:4, and having at least one substitution relative to SEQ ID NO:4 of an amino acid residue described herein, where the variant has greater enzymatic activity than that of the enzyme set forth in SEQ ID NO: 4. Also provided are polynucleotides encoding the β-glucosidase variants, expression vectors comprising the polynucleotides, and host cells transformed with the expression vectors.

The invention also provides methods for producing at least one β-glucosidase variants (i.e., variant polypeptides) by culturing a host cell transformed with at least one polynucleotide encoding at least one β-glucosidase variant under conditions suitable for the expression of the β-glucosidase variant(s). In some embodiments, the β-glucosidase variant(s) is/are recovered from the culture medium or from the transformed and cultured cells.

The invention also provides enzyme compositions comprising an isolated or recombinant *T. aurantiacus* β-glucosidase variant. In some embodiments, the enzyme composition also includes at least one additional cellulase enzyme. In some additional embodiments, the enzyme composition comprises at least one additional cellulase and/or at least one additional enzyme.

In some embodiments, the present invention provides methods for converting a biomass substrate (e.g., cellobiose), to a fermentable sugar by contacting a β-glucosidase variant with the biomass substrate under conditions suitable for the production of the fermentable sugar. In some embodiments, the biomass substrate is maintained in a medium containing cells expressing at least one β-glucosidase variant. In some embodiments, the recombinant host cell expressing at least one β-glucosidase variant also expresses at least one other recombinant cellulase enzyme and/or at least one other recombinant or native enzyme. In some embodiments, the biomass substrate is optionally pretreated before contacting the substrate with a β-glucosidase variant or more than one β-glucosidase variant.

In some embodiments, the present invention provides a variant β-glucosidase comprising an amino acid sequence that is at least about 70% identical to SEQ ID NO:2 having at least one modification or which is encoded by a nucleic acid that hybridizes under stringent conditions to the complement of SEQ ID NO:1, wherein the variant has greater enzymatic activity than SEQ ID NO:2. In some embodiments, the variant β-glucosidase comprises at least one substitution of an amino acid residue at a position selected from A478, D203, E344, F287, H684, K100, K291, K342, K456, K54, L149, N355, N650, P739, P790, R330, S408, S86, T150, Y331, Y641, Y679, and Y746.

In some alternative embodiments, the present invention provides a variant β-glucosidase comprising an amino acid sequence that is at least about 70% identical to SEQ ID NO:4, and having at least one modification relative to SEQ ID NO:4 of an amino acid residue described herein, where the variant has greater enzymatic activity than SEQ ID NO: 4. In some embodiments, the variant β-glucosidase comprises at least one substitution of an amino acid residue at a position selected from A479, D204, E345, F288, H685, K101, K292, K343, K457, K55, L150, M1, N356, N651, P740, P791, R331, S409, S87, T151, Y332, Y642, Y680, and Y747. In some embodiments, the variant β-glucosidase comprises at least one amino acid substitution selected from T151S, Y642N, N651K, K101R, T151S, K343R, N356S, S409N, Y642N, N651K, K101R, T151S, K343R, N356S, S409N, Y642N, N651K, M1T, K55R, K101R, T151S, R331K, Y332C, K343R, N356S, S409N, Y642N, M1T, K101R, T151S, K292E, K343R, S409N, Y642N, P740S, M1T, T151S, K343R, S409N, A479V, Y642N, Y680F, L150V, T151S, K343R, S409N, K457R, Y642N, N651K, 587N, T151S, F288Y, Y642N, and N651K. In some further embodiments, the variant β-glucosidase comprises at least one amino acid substitution selected from T151S, Y642N, N651K, D204G, K292I, E345V, Y747C, H685Y, and P791T. In some additional embodiments, the polynucleotide sequence encoding the variant β-glucosidase comprises at least one base change selected from t1044c, t1656a, t2052c, and a2520g. In yet some further embodiments, the polynucleotide sequence encoding the β-glucosidase variant comprises at least one base change selected from a1515g, g165a, t651c, and 726c. In some additional embodiments, the variant β-glucosidase comprises at least one amino acid substitution selected from the substitution sets T151S-Y642N-N651K, D204G-K292I, E345V-Y747C, and H685Y-P791T. In some further embodiments, the variant β-glucosidase comprises at least one amino acid substitution is selected from the substitution sets T151S-Y642N-N651K, K101R-T151S-K343R-N356S-S409N-Y642N-N651K, M1T-K55R-K101R-T151S-R331K-Y332C-K343R-N356S-S409N-Y642N, M1T-K101R-T151S-K292E-K343R-S409N-Y642N-P740S, M1T-T151S-K343R-S409N-A479V-Y642N-Y680F, L150V-T151S-K343R-S409N-K457R-Y642N-N651K, and S87N-T151S-F288Y-Y642N-N651K.

The present invention also provides polynucleotide sequences encoding the β-glucosidase variants provided herein. The present invention also provides expression vectors comprising at least one polynucleotide sequence encoding at least one β-glucosidase variant. The present invention further provides host cells comprising the expression vectors comprising at least one polynucleotide sequence encoding at least one β-glucosidase variant.

The present invention also provides methods for producing at least one β-glucosidase variant comprising providing a host cell and an expression vector comprising at least one polynucleotide sequence encoding at least one β-glucosidase variant, introducing the expression vector into the host cell to produced a transformed host cell, and culturing the transformed host cell under conditions such that at least one β-glucosidase variant is expressed. It is contemplated that a plurality of host cells will find use in the present invention. In some embodiments, one expression vector is used, while in other embodiments more than one expression vector is used. Also, in some embodiments, the expression vectors comprise a single β-glucosidase variant, while in some other embodiments, the expression vectors comprise more than one β-glucosidase variant. Furthermore, in some embodiments, the expression vectors comprise at least one polynucleotide sequence that encodes at least one additional enzyme, including but not limited to at least one cellulase. In some embodiments, the methods further comprise the step of isolating the β-glucosidase variant produced. In some additional embodiments, the methods further comprise isolating at least one additional enzyme produced using the methods.

The present invention also provides compositions comprising at least one β-glucosidase variant. In some embodiments, the compositions comprise at least one buffer, surfactant, and/or scouring and/or other agent. In some embodiments, the compositions further comprise at least one additional enzyme. In some embodiments, the at least one additional enzyme is a cellulase. It is contemplated that the β-glucosidase variants provided by the present invention will find use in numerous suitable compositions. Indeed, it is intended that the β-glucosidase variants provided herein will find use in various applications.

The present invention also provides methods of converting biomass substrate to produce at least one fermentable sugar, comprising providing at least one β-glucosidase variant and biomass substrate, and exposing the biomass substrate to the at least one β-glucosidase variant under conditions such that the at least one β-glucosidase variant converts the biomass substrate into at least one fermentable sugar. In some embodiments, the fermentable sugar produced from the biomass substrate by the action of the β-glucosidase variant is glucose. In some additional embodiments, sugars other than glucose are produced. In some other embodiments, mixtures of sugars are produced. In some embodiments, mixtures of sugars including glucose are produced. In some other embodiments, combinations comprising mixtures of sugars other than glucose are produced. In some additional embodiments, the biomass substrate is pretreated before exposing the biomass substrate to at least one β-glucosidase variant.

BRIEF DESCRIPTION OF THE FIGURES

FIG. 1 provides a graph showing glucose production from AVICEL® cellulose, using *C. lucknowense* (C1) fermentation broth, supplemented with β-glucosidase. In this graph, 'C1' and 'TaB6' represent samples from C1-fungus fermentation broth and *T. aurantiacus* Bgl1-derived variant TaB6, respectively. The reaction conditions were 65° C., pH 5, 200 g/L AVICEL® cellulose, 100 g/L xylose. The amount of β-glucosidase added was based on gram dry weight powder, not amount of active β-glucosidase.

DESCRIPTION OF THE INVENTION

The present invention provides compositions and methods for the expression of recombinant β-glucosidase variants, as well as their use in the production of fermentable sugars from cellulosic biomass.

DEFINITIONS

The following definitions are provided to assist the reader. Unless otherwise defined, all technical, scientific and other terms of art are intended to have the meanings commonly understood by those of skill in the molecular biology, fermentation, microbiology, and related arts. In some cases, terms with commonly understood meanings are defined herein for clarity and/or for ready reference, and the inclusion of such definitions herein should not necessarily be construed to represent a substantial difference over the definition of the term as generally understood in the art.

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Although any methods and materials similar or equivalent to those described herein can be used in the practice or testing of the present invention, some preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" includes the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, the terms "isolated" and "purified" are used to refer to a molecule (e.g., an isolated nucleic acid, polypeptide, etc.) or other component that is removed (i.e., partially or completely separated) from at least one other component with which it is naturally associated. (e.g., other proteins, nucleic acids, cells, synthetic reagents, etc.).

As used herein, the term "derivative enzyme" (e.g., enzyme derivative" or "β-glucosidase derivative") refer to an enzyme that retains the characteristic activity of the wild-type, native or reference enzyme (e.g., β-glucosidase), to the extent that the derivative is useful for similar purposes as the wild-type, native or reference form. "Functional derivatives" of β-glucosidase enzymes encompass naturally-occurring, synthetic or recombinantly produced polypeptides or peptide fragments that have the general characteristics of the β-glucosidases of the present invention.

As used herein, the term "overexpress" is intended to encompass increasing the expression of a protein to a level greater than the cell normally produces. It is intended that the term encompass overexpression of endogenous, as well as heterologous proteins.

As used herein, the term "cellobiose" has its ordinary meaning and refers to a disaccharide with the formula $C_{12}H_{22}O_{11}$.

As used herein, the term "cellulase" refers to a category of enzymes capable of hydrolyzing cellulose (β-1,4-glucan or β-D-glucosidic linkages) to shorter oligosaccharides, cellobiose and/or glucose.

As used herein, the terms "β-glucosidase" or "cellobiase" are used interchangeably and refer to a β-D-glucoside glucohydrolase which catalyzes the hydrolysis of a sugar dimer, including but not limited to cellobiose, with the release of a corresponding sugar monomer. In some embodiments, a β-glucosidase is a β-glucosidase glucohydrolase of the classification E.C. 3.2.1.21 which catalyzes the hydrolysis of cellobiose to glucose. Some β-glucosidases have the ability to also hydrolyze β-D-galactosides, β-L-arabinosides and/or β-D-fucosides and further some β-glucosidases can act on α-1,4-substrates such as starch. β-glucosidase activity may be measured by methods any suitable method known in the art, including the assays described herein below.

As used herein, the term "β-glucosidase polypeptide" refers to a polypeptide having β-glucosidase activity.

As used herein, the term "β-glucosidase polynucleotide" refers to a polynucleotide encoding a polypeptide having β-glucosidase activity.

As used herein, "cellulolytic activity" encompasses exoglucanase activity (CBH), endoglucanase (EG) activity and/or β-glucosidase activity.

As used herein, the terms "exoglucanase", "exo-cellobiohydrolase" or "CBH" refer to a group of cellulase enzymes classified as E.C. 3.2.1.91. These enzymes hydrolyze cellobiose from the reducing or non-reducing end of cellulose.

As used herein, the terms "endoglucanase" or "EG" refer to a group of cellulase enzymes classified as E.C. 3.2.1.4. These enzymes hydrolyze internal β-1,4 glucosidic bonds of cellulose.

As used herein, the terms "wildtype" and "wild-type" as applied to a polypeptide (protein) refer to a polypeptide (protein) expressed by a naturally occurring microorganism such as bacteria or filamentous fungi. As applied to a microorganism, the terms "wildtype" and "wild-type" refer to the native, non-recombinant microorganism.

As used herein, the terms "wild-type gene" and "wild-type polynucleotide sequence" refer to a polynucleotide sequence that is native or naturally-occurring in a host cell. In some embodiments, the wild-type sequence refers to a sequence of interest that is the starting point of a protein engineering project. The wild-type sequence may encode either a homologous (i.e., a protein that the cell would produce without intervention) or heterologous protein (i.e., a protein that the cell would not produce but for the intervention).

As used herein, the term "naturally occurring enzyme" refers to an enzyme having an unmodified amino acid sequence (i.e., a sequence that is identical to that found in nature). Naturally occurring enzymes include those enzymes that are naturally expressed.

As used herein, the terms "modified polynucleotide sequence," "modified nucleotide sequence," and "modified genes" refer to a nucleotide sequence that includes a deletion, insertion, substitution, or interruption of naturally occurring or starting nucleic acid sequence of interest. In some embodiments, the expression product of the modified sequence is a truncated protein (e.g., if the modification is a deletion or interruption of the starting sequence). In some embodiments, the truncated protein retains biological activity. In some alternative embodiments, the expression product of the modified sequence is an elongated protein (e.g., modifications comprise insertion(s) into the starting nucleic acid sequence). In some embodiments, an insertion leads to a truncated protein (e.g., when the insertion results in the formation of a stop codon). Thus, an insertion may result in either a truncated protein or an elongated protein as an expression product. In some embodiments, the modification is a substitution of at least one nucleic acid residue in the starting sequence.

As used herein, "modified polypeptide sequence" and "modified protein" refer to a polypeptide sequence that includes a deletion, insertion, substitution, or interruption of a naturally occurring or starting polypeptide sequence of interest. In some embodiments, the modified sequence is a truncated protein (e.g., if the modification is a deletion or interruption of the starting sequence). In some embodiments, the truncated protein retains biological activity. In some alternative embodiments, the modified sequence is an elongated protein (e.g., modifications comprise insertion(s) in the starting sequence). In some embodiments, the modification is a substitution of at least one amino acid residue in the starting sequence.

As used herein, "protein of interest" and "polypeptide of interest" refer to a protein/polypeptide that is desired and/or being assessed.

As used herein, the terms "starting sequence of interest" and "starting sequence" refer to either a nucleic acid (e.g., "starting polynucleotide of interest") or an amino acid sequence (e.g., "starting polypeptide of interest") that serves as the starting point for comparison or for engineering purposes. In some embodiments, the starting sequence is referred to as a "reference sequence." In some embodiments, the starting sequence is a wild-type sequence, while in other embodiments, the starting sequence is a modified sequence (i.e., a recombinant sequence).

As used herein, the terms "β-glucosidase variant," "β-glucosidase variant polypeptide," and "β-glucosidase variant protein" refer to a β-glucosidase polypeptide or polynucleotide encoding a β-glucosidase comprising one or more modifications (e.g., substitutions, deletions, insertions, and/or truncations) of one or more specific amino acid residues or of one or more specific nucleotides or codons in the polypeptide or polynucleotide relative to wildtype β-glucosidase (Bgl1) polypeptide or wildtype polynucleotide. In some embodiments, the β-glucosidase variant is a T. aurantiacus β-glucosidase variant.

As used herein, a "reference β-glucosidase sequence" refers to a defined sequence used as a basis for a sequence comparison or as a "starting sequence," such as SEQ ID NO:2 or SEQ ID NO:4. In some embodiments, a reference β-glucosidase sequence comprises a subset of a larger sequence. Generally, a reference sequence is at least about 25 amino acid residues in length, at least about 50 residues in length, at least about 100 residues in length, at least about 150 residues in length at least about 200 residues in length, at least about 300 residues in length, at least about 350 residues in length, at least about 500 residues in length, at least about 600 residues in length, at least about 700 residues in length, or the full length of the polypeptide.

As used herein, the term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. A nucleic acid (such as a polynucleotide), a polypeptide, or a cell is "recombinant" when it is artificial or engineered, or derived from or contains an artificial or engineered protein or nucleic acid. For example, a polynucleotide that is inserted into a vector or any other heterologous location, (e.g., in a genome of a recombinant organism), such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature (e.g., a variant of a naturally occurring gene), is recombinant.

As used herein, an "improved property" refers to a β-glucosidase polypeptide that exhibits an improvement in any property as compared to the wildtype T. aurantiacus β-glucosidase (Bgl1) (SEQ ID NO: 2). Improved properties include, but are not limited to increased protein expression, thermoactivity, thermostability, pH activity, pH stability, product specificity, increased specific activity, substrate specificity, increased resistance to substrate or end-product inhibition, altered pH/temperature profile, and/or chemical stability.

As used herein, a "variant with improved β-glucosidase activity," refers to a variant displaying an increase, relative to a reference β-glucosidase, in the amount of substrate hydrolysis that occurs in a specified time under specified reaction conditions. β-glucosidase activity can be measured using a variety of methods known in the art, including but not limited to the cellobiose assays described herein. To compare the β-glucosidase activity of two recombinantly expressed proteins, the specific activity (i.e., the enzymatic activity per mole enzyme or enzymatic activity per gram enzyme) can be compared. Alternatively, cells expressing and secreting the recombinant proteins are cultured under the same conditions and the β-glucosidase activity per volume culture medium compared.

The terms "percent identity," "% identity," "percent identical," and "% identical" are used interchangeably herein to refer to the percent amino acid sequence identity that is obtained by ClustalW analysis (e.g., version W 1.8 available from European Bioinformatics Institute, Cambridge, UK), counting the number of identical matches in the alignment and dividing such number of identical matches by the length of the reference sequence, and using the following default ClustalW parameters to achieve slow/accurate pairwise optimal alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences Amino acid substitution matrices and their use in quantifying the similarity between two sequences are well-known in the art (See e.g., Dayhoff et al., Atlas Prot. Seq. Struct., 5, Suppl. 3:345-352 [1978]; and Henikoff et al., Proc. Natl. Acad. Sci., 89:10915-10919 [1992], both of which are incorporated herein by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul, et al., Nucl. Acids Res., 25:3389-3402 [1997], incorporated herein by reference), and made available to the public at the National Center for Biotechnology Information Website. Optimal alignments, including multiple alignments can be prepared using readily available programs such as PSI-BLAST; Altschul et al., supra).

As used herein, the terms "corresponding to," "in reference to," and "relative to," when used in the context of the numbering of a given amino acid or polynucleotide sequence, refer to the numbering of the residues of a specified reference sequence when the given amino acid or polynucleotide sequence is compared to a reference sequence.

An amino acid or nucleotide base "position" is denoted by a number that sequentially identifies each amino acid (or nucleotide base) in the reference sequence based on its position relative to the N-terminus. Due to deletions, insertions, truncations, fusions, and the like that must be taken into account when determining an optimal alignment, the amino acid residue number in a test sequence determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. Hybridization methods are well known in the art and any suitable method finds use in the present invention. For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

As used herein, the terms "culturing" and "cultivation" refer to growing a population of microbial cells under suitable conditions in a liquid, semi-solid, or solid medium. In some embodiments, "culturing" refers to fermentative bioconversion of a cellulosic substrate to an end-product.

When used in reference to enzymatic activity, the term "contacting" refers to the placing of an enzyme in sufficiently close proximity to its respective substrate to enable the enzyme to convert the substrate to a product. Those skilled in the art recognize that mixing a solution of an enzyme with the respective substrate will effect "contacting." "Contacting" also encompasses incubating a cell secreting an enzyme in a medium containing an enzyme substrate.

As used herein, a β-glucosidase variant polypeptide is "enzymatically active" when it has β-glucosidase activity.

As used herein, the terms "transformed" and "transformation" when used in reference to a cell means that the cell has a non-native nucleic acid sequence integrated into its genome or as an episomal plasmid that is maintained through multiple generations.

As used herein, the term "introduced" in the context of inserting a nucleic acid sequence into a cell means that the cell has been transfected, transduced or transformed (collectively "transformed") or the nucleic acid has otherwise been incorporated into the cell's genome or is maintained as an episome within the cell.

As used herein, the term "operably linked" refers to a configuration in which a control sequence is appropriately placed at a position relative to the coding sequence of a DNA sequence such that the control sequence influences the expression of a polypeptide.

As used herein, the term "coding sequence" is intended to encompass nucleotide sequences that directly encode the amino acid sequences of their protein products. The boundaries of coding sequences are generally determined by an open reading frame, which usually begin with the ATG start codon. In some embodiments, the coding sequences comprise DNA, cDNA, and/or recombinant nucleotide sequences.

A promoter sequence, signal peptide, or other sequence is "heterologous", when it is operably linked to a nucleic acid or protein sequence with which the promoter, signal peptide or other sequence is not associated in nature.

As used herein, the term "expression" includes any step involved in the production of the polypeptide including, but not limited to, transcription, post-transcriptional modification, translation, post-translational modification, and secretion.

As used herein, the term "expression vector" refers herein to a DNA molecule, linear or circular, that comprises a segment encoding a polypeptide of the invention, and which is operably linked to additional segments that provide for its transcription.

As used herein, the term "pre-protein" refers to a protein including an amino-terminal signal peptide (or leader sequence) region attached. The signal peptide is cleaved from the pre-protein by a signal peptidase prior to secretion to produce the "mature" or "secreted" protein.

As used herein, a "start codon" is the ATG codon that encodes the first amino acid residue (methionine) of a protein.

The following nomenclature finds use in describing substitutions in a reference sequence relative to a reference sequence or a variant polypeptide or nucleic acid sequence: "R-#-V," where # refers to the position in the reference sequence, R refers to the amino acid (or base) at that position in the reference sequence, and V refers to the amino acid (or base) at that position in the variant sequence. For example, for a variant polypeptide described with reference to SEQ ID NO: 4, "A479V" indicates that in the variant polypeptide, the alanine at position 479 of the reference sequence is replaced by valine, with amino acid position being determined by optimal alignment of the variant sequence with SEQ ID NO:4.

The following conventions are used to describe amino acid positions in Bgl1 variants. Amino acid positions are numbered in relation the reference sequence SEQ ID NO:2, which is the sequence of the wild-type (WT) Bgl1 secreted protein or SEQ ID NO:4, the $WT^M$ form described herein. SEQ ID NO:6 provides the amino acid sequence of the WT mature protein, including the signal peptide. SEQ ID NO:1 provides the DNA sequence of the WT mature protein, while SEQ ID NO:3 provides the DNA sequence of the $WT^M$ protein, and SEQ ID NO:5 provides the DNA sequence of the WT sequence, including the signal peptide sequence.

The polynucleotide encoding wild-type *T. aurantiacus* β-glucosidase protein (secreted form) is provided below:

```
                                              (SEQ ID NO: 1)
AAGGATGACTTGGCCTACTCGCCGCCTTTCTACCCGTCGCCGTGGATGGA

CGGAAACGGAGAGTGGGCGGAGGCCTACCGCAGGGCTGTCGACTTCGTCT

CGCAGCTGACCCTCGCGGAGAAGGTCAACCTGACGACCGGTGTCGGGTGG

ATGCAGGAGAAATGTGTCGGTGAAACGGGCAGCATTCCGAGGCTGGGGTT
```

```
CCGTGGACTGTGCCTCCAAGACTCGCCCCTTGGTGTCAGATTTGCTGACT
ACGTTTCTGCCTTCCCCGCCGGTGTCAACGTCGCTGCAACGTGGGATAAG
AACCTCGCCTACCTTCGTGGGAAGGCGATGGGTGAGGAACACCGTGGTAA
GGGCGTCGACGTCCAGCTGGGACCTGTCGCCGGCCCTCTTGGCAGACACC
CCGACGGTGGCAGAAACTGGGAGGGTTTCTCTCCTGACCCCGTCCTGACC
GGTGTGCTTATGGCGGAGACGATCAAGGGTATCCAGGACGCCGGTGTGAT
TGCTTGCGCCAAGCACTTCATTGGTAACGAGATGGAGCACTTCCGGCAAG
CCAGTGAGGCTGTTGGTTATGGTTTCGATATTACCGAGAGTGTCAGCTCA
AATATCGACGACAAGACGCTTCACGAGCTGTACCTTTGGCCCTTTGCGGA
TGCTGTTCGCGCTGGCGTTGGTTCGTTCATGTGCTCCTACAACCAGGTTA
ACAACAGCTACAGCTGCTCGAACAGCTACCTCCTAAACAAGTTGCTCAAA
TCGGAGCTTGATTTTCAGGGCTTCGTGATGAGTGACTGGGGAGCGCACCA
CAGCGGCGTTGGAGCTGCCCTGGCTGGCCTTGACATGTCGATGCCAGGAG
ACACCGCCTTTGGTACCGGCAAATCCTTCTGGGGAACCAACCTGACCATC
GCCGTTCTCAACGGCACTGTTCCGGAATGGCGTGTGGATGACATGGCTGT
TCGCATCATGGCGGCCTTTTACAAGGTTGGTCGCGACCGTTACCAGGTGC
CGGTCAACTTCGACTCGTGGACGAAGGATGAATACGGTTACGAGCACGCA
CTGGTTGGCCAGAACTATGTCAAGGTCAATGACAAGGTGGATGTTCGTGC
CGACCATGCGGACATCATCCGTCAAATTGGGTCTGCTAGTGTTGTCCTTC
TTAAGAACGATGGAGGACTCCCATTGACCGGCTATGAAAAGTTCACCGGA
GTTTTTGGAGAGGATGCCGGATCGAACCGTTGGGCGCTGACGGCTGCTC
TGATCGTGGTTGCGACAACGGCACGTTGGCAATGGGTTGGGGCAGTGGCA
CTGCTGACTTCCCCTACCTTGTCACTCCCGAGCAGGCAATCCAGAATGAA
ATCCTTTCCAAGGGGAAGGGGTTAGTGAGTGCTGTCACCGACAATGGTGC
CCTGGACCAGATGGAACAGGTTGCGTCTCAGGCCAGCGTTTCTATCGTTT
TCGTCAACGCCGACTCTGGTGAAGGCTACATCAACGTTGATGGCAACGAA
GGTGATCGGAAGAACCTCACCCTCTGGAAGGGAGGCGAGGAGGTGATCAA
GACTGTTGCAGCCAACTGCAACAACACCATTGTTGTGATGCACACTGTGG
GACCTGTCTTGATCGATGAGTGGTATGACAACCCCAACGTCACCGCCATC
GTCTGGGCCGGTCTTCCAGGCCAGGAGAGCGGCAACAGTCTCGTCGATGT
GCTCTACGGCCGTGTCAGCCCCGGAGGAAAGACGCCGTTTACGTGGGAA
AGACTCGCGAGTCGTACGGCGCTCCTCTGCTCACCAAACCCAACAACGGC
AAGGGTGCCCCCCAGGACGACTTCACCGAGGGCGTCTTCATCGACTACAG
AAGGTTCGACAAGTACAACGAGACGCCCATCTATGAGTTCGGGTTTGGTC
TGAGTTATACCACTTTTGAATACTCGGACATCTACGTCCAGCCCCTTAAC
GCACGACCTTACACCCCAGCCTCCGGCAGCACCAAGGCGGCTCCTACCTT
TGGGAACATCAGCACGGACTATGCAGATTACTTGTACCCTGAGGATATAC
ACAAGGTCCCATTATACATCTATCCTTGGCTTAACACGACGGACCCGAAG
AAGTCCTCCGGCGATCCCGACTACGGAATGAAGGCCGAGGACTACATCCC
ATCTGGCGCGACTGATGGATCTCCTCAGCCCATCCTTCCGGCAGGCGGTG
CTCCTGGTGGCAACCCGGGTCTCTATGATGAGATGTACAGGGTATCTGCA
ATCATCACCAACACCGGTAACGTTGTTGGTGATGAGGTTCCTCAGCTGTA
TGTCTCTCTTGGTGGTCCAGATGACCCCAAGGTCGTGCTCCGCAACTTTG
ACCGCATCACGCTCCACCCCGGCCAGCAGACAATGTGGACCACGACATTG
ACGCGACGCGATATCTCGAACTGGGACCCTGCCTCCCAGAATTGGGTTGT
GACCAAATATCCCAAGACAGTCTACATCGGCAGCTCTTCGCGGAAACTGC
ACCTGCAGGCACCGCTTCCCCCTTAC
```

The polypeptide sequence of the wild-type T. aurantiacus β-glucosidase protein (secreted form) is provided below:

(SEQ ID NO: 2)
KDDLAYSPPFYPSPWMDGNGEWAEAYRRAVDFVSQLTLAEKVNLTTGVGW
MQEKCVGETGSIPRLGFRGLCLQDSPLGVRFADYVSAFPAGVNVAATWDK
NLAYLRGKAMGEEHRGKGVDVQLGPVAGPLGRHPDGGRNWEGFSPDPVLT
GVLMAETIKGIQDAGVIACAKHFIGNEMEHFRQASEAVGYGFDITESVSS
NIDDKTLHELYLWPFADAVRAGVGSFMCSYNQVNNSYSCSNSYLLNKLLK
SELDFQGFVMSDWGAHHSGVGAALAGLDMSMPGDTAFGTGKSFWGTNLTI
AVLNGTVPEWRVDDMAVRIMAAFYKVGRDRYQVPVNFDSWTKDEYGYEHA
LVGQNYVKVNDKVDVRADHADIIRQIGSASVVLLKNDGGLPLTGYEKFTG
VFGEDAGSNRWGADGCSDRGCDNGTLAMGWGSGTADFPYLVTPEQAIQNE
ILSKGKGLVSAVTDNGALDQMEQVASQASVSIVFVNADSGEGYINVDGNE
GDRKNLTLWKGGEEVIKTVAANCNNTIVVMHTVGPVLIDEWYDNPNVTAI
VWAGLPGQESGNSLVDVLYGRVSPGGKTPFTWGKTRESYGAPLLTKPNNG
KGAPQDDFTEGVFIDYRRFDKYNETPIYEFGFGLSYTTFEYSDIYVQPLN
ARPYTPASGSTKAAPTFGNISTDYADYLYPEDIHKVPLYIYPWLNTTDPK
KSSGDPDYGMKAEDYIPSGATDGSPQPILPAGGAPGGNPGLYDEMYRVSA
IITNTGNVVGDEVPQLYVSLGGPDDPKVVLRNFDRITLHPGQQTMWTTTL
TRRDISNWDPASQNWVVTKYPKTVYIGSSSRKLHLQAPLPPY

The polynucleotide sequence encoding T. aurantiacus β-glucosidase protein (WT$^M$ form) is shown below:

(SEQ ID NO: 3)
```
ATGAAGGATGACTTGGCCTACTCGCCGCCTTTCTACCCGTCGCCGTGGAT
GGACGGAAACGGAGAGTGGGCGGAGGCCTACCGCAGGGCTGTCGACTTCG
TCTCGCAGCTGACCCTCGCGGAGAAGGTCAACCTGACGACCGGTGTCGGG
TGGATGCAGGAGAAATGTGTCGGTGAAACGGGCAGCATTCCGAGGCTGGG
GTTCCGTGGACTGTGCCTCCAAGACTCGCCCCTTGGTGTCAGATTTGCTG
ACTACGTTTCTGCCTTCCCCGCCGGTGTCAACGTCGCTGCAACGTGGGAT
AAGAACCTCGCCTACCTTCGTGGGAAGGCGATGGGTGAGGAACACCGTGG
TAAGGGCGTCGACGTCCAGCTGGGACCTGTCGCCGGCCCTCTTGGCAGAC
ACCCCGACGGTGGCAGAAACTGGGAGGGTTTCTCTCCTGACCCCGTCCTG
ACCGGTGTGCTTATGGCGGAGACGATCAAGGGTATCCAGGACGCCGGTGT
```

-continued
```
GATTGCTTGCGCCAAGCACTTCATTGGTAACGAGATGGAGCACTTCCGGC
AAGCCAGTGAGGCTGTTGGTTATGGTTTCGATATTACCGAGAGTGTCAGC
TCAAATATCGACGACAAGACGCTTCACGAGCTGTACCTTTGGCCCTTTGC
GGATGCTGTTCGCGCTGGCGTTGGTTCGTTCATGTGCTCCTACAACCAGG
TTAACAACAGCTACAGCTGCTCGAACAGCTACCTCCTAAACAAGTTGCTC
AAATCGGAGCTTGATTTTCAGGGCTTCGTGATGAGTGACTGGGGAGCGCA
CCACAGCGGCGTTGGAGCTGCCCTGGCTGGCCTTGACATGTCGATGCCAG
GAGACACCGCCTTTGGTACCGGCAAATCCTTCTGGGGAACCAACCTGACC
ATCGCCGTTCTCAACGGCACTGTTCCGGAATGGCGTGTGGATGACATGGC
TGTTCGCATCATGGCGGCCTTTTACAAGGTTGGTCGCGACCGTTACCAGG
TGCCGGTCAACTTCGACTCGTGGACGAAGGATGAATACGGTTACGAGCAC
GCACTGGTTGGCCAGAACTATGTCAAGGTCAATGACAAGGTGGATGTTCG
TGCCGACCATGCGGACATCATCCGTCAAATTGGGTCTGCTAGTGTTGTCC
TTCTTAAGAACGATGGAGGACTCCCATTGACCGGCTATGAAAAGTTCACC
GGAGTTTTTGGAGAGGATGCCGGATCGAACCGTTGGGGCGCTGACGGCTG
CTCTGATCGTGGTTGCGACAACGGCACGTTGGCAATGGGTTGGGGCAGTG
GCACTGCTGACTTCCCCTACCTTGTCACTCCCGAGCAGGCAATCCAGAAT
GAAATCCTTTCCAAGGGGAAGGGGTTAGTGAGTGCTGTCACCGACAATGG
TGCCCTGGACCAGATGGAACAGGTTGCGTCTCAGGCCAGCGTTTCTATCG
TTTTCGTCAACGCCGACTCTGGTGAAGGCTACATCAACGTTGATGGCAAC
GAAGGTGATCGGAAGAACCTCACCCTCTGGAAGGGAGGCGAGGAGGTGAT
CAAGACTGTTGCAGCCAACTGCAACAACACCATTGTTGTGATGCACACTG
TGGGACCTGTCTTGATCGATGAGTGGTATGACAACCCCAACGTCACCGCC
ATCGTCTGGGCCGGTCTTCCAGGCCAGGAGAGCGGCAACAGTCTCGTCGA
TGTGCTCTACGCCGTGTCAGCCCCGGAGGAAAGACGCCGTTTACGTGGG
GAAAGACTCGCGAGTCGTACGGCGCTCCTCTGCTCACCAAACCCAACAAC
GGCAAGGGTGCCCCCCAGGACGACTTCACCGAGGGCGTCTTCATCGACTA
CAGAAGGTTCGACAAGTACAACGAGACGCCCATCTATGAGTTCGGGTTTG
GTCTGAGTTATACCACTTTTGAATACTCGGACATCTACGTCCAGCCCCTT
AACGCACGACCTTACACCCCAGCCTCCGGCAGCACCAAGGCGGCTCCTAC
CTTTGGGAACATCAGCACGGACTATGCAGATTACTTGTACCCTGAGGATA
TACACAAGGTCCCATTATACATCTATCCTTGGCTTAACACGACGGACCCG
AAGAAGTCCTCCGGCGATCCCGACTACGGAATGAAGGCCGAGGACTACAT
CCCATCGGCGCGACTGATGGATCTCCTCAGCCCATCCTTCCGGCAGGCG
GTGCTCCTGGTGGCAACCCGGGTCTCTATGATGAGATGTACAGGGTATCT
GCAATCATCACCAACACCGGTAACGTTGTTGGTGATGAGGTTCCTCAGCT
GTATGTCTCTCTTGGTGGTCCAGATGACCCCAAGGTCGTGCTCCGCAACT
TTGACCGCATCACGCTCCACCCCGGCCAGCAGACAATGTGGACCACGACA
TTGACGCGACGCGATATCTCGAACTGGGACCCTGCCTCCCAGAATTGGGT
TGTGACCAAATATCCCAAGACAGTCTACATCGGCAGCTCTTCGCGGAAAC
TGCACCTGCAGGCACCGCTTCCCCCTTAC
```

The polypeptide sequence of the *T. aurantiacus* β-glucosidase protein WT$^M$ form is shown below:

(SEQ ID NO: 4)
```
MKDDLAYSPPFYPSPWMDGNGEWAEAYRRAVDFVSQLTLAEKVNLTTGVG
WMQEKCVGETGSIPRLGFRGLCLQDSPLGVRFADYVSAFPAGVNVAATWD
KNLAYLRGKAMGEEHRGKGVDVQLGPVAGPLGRHPDGGRNWEGFSPDPVL
TGVLMAETIKGIQDAGVIACAKHFIGNEMEHFRQASEAVGYGFDITESVS
SNIDDKTLHELYLWPFADAVRAGVGSFMCSYNQVNNSYSCSNSYLLNKLL
KSELDFQGFVMSDWGAHHSGVGAALAGLDMSMPGDTAFGTGKSFWGTNLT
IAVLNGTVPEWRVDDMAVRIMAAFYKVGRDRYQVPVNFDSWTKDEYGYEH
ALVGQNYVKVNDKVDVRADHADIIRQIGSASVVLLKNDGGLPLTGYEKFT
GVFGEDAGSNRWGADGCSDRGCDNGTLAMGWGSGTADFPYLVTPEQAIQN
EILSKGKGLVSAVTDNGALDQMEQVASQASVSIVFVNADSGEGYINVDGN
EGDRKNLTLWKGGEEVIKTVAANCNNTIVVMHTVGPVLIDEWYDNPNVTA
IVWAGLPGQESGNSLVDVLYGRVSPGGKTPFTWGKTRESYGAPLLTKPNN
GKGAPQDDFTEGVFIDYRRFDKYNETPIYEFGFGLSYTTFEYSDIYVQPL
NARPYTPASGSTKAAPTFGNISTDYADYLYPEDIHKVPLYIYPWLNTTDP
KKSSGDPDYGMKAEDYIPSGATDGSPQPILPAGGAPGGNPGLYDEMYRVS
AIITNTGNVVGDEVPQLYVSLGGPDDPKVVLRNFDRITLHPGQQTMWTTT
LTRRDISNWDPASQNWVVTKYPKTVYIGSSSRKLHLQAPLPPY
```

The polynucleotide encoding the *T. aurantiacus* β-glucosidase pre-protein is shown below:

(SEQ ID NO: 5)
```
ATGAGGCTTGGGTGGCTGGAGCTGGCCGTCGCGGCGGCCGCGACCGTCGC
CAGCGCCAAGGATGACTTGGCCTACTCGCCGCCTTTCTACCCGTCGCCGT
GGATGGACGGAAACGGAGAGTGGGCGGAGGCCTACCGCAGGGCTGTCGAC
TTCGTCTCGCAGCTGACCCTCGCGGAGAAGGTCAACCTGACGACCGGTGT
CGGGTGGATGCAGGAGAAATGTGTCGGTGAAACGGGCAGCATTCCGAGGC
TGGGGTTCCGTGGACTGTGCCTCCAAGACTCGCCCCTTGGTGTCAGATTT
GCTGACTACGTTTCTGCCTTCCCCGCCGGTGTCAACGTCGCTGCAACGTG
GGATAAGAACCTCGCCTACCTTCGTGGGAAGGCGATGGGTGAGGAACACC
GTGGTAAGGGCGTCGACGTCCAGCTGGGACCTGTCGCCGGCCCTCTTGGC
AGACACCCCGACGGTGGCAGAAACTGGGAGGGTTTCTCTCCTGACCCCGT
CCTGACCGGTGTGCTTATGGCGGAGACGATCAAGGGTATCCAGGACGCCG
GTGTGATTGCTTGCGCCAAGCACTTCATTGGTAACGAGATGGAGCACTTC
CGGCAAGCCAGTGAGGCTGTTGGTTATGGTTTCGATATTACCGAGAGTGT
CAGCTCAAATATCGACGACAAGACGCTTCACGAGCTGTACCTTTGGCCCT
TTGCGGATGCTGTTCGCGCTGGCGTTGGTTCGTTCATGTGCTCCTACAAC
CAGGTTAACAACAGCTACAGCTGCTCGAACAGCTACCTCCTAAACAAGTT
GCTCAAATCGGAGCTTGATTTTCAGGGCTTCGTGATGAGTGACTGGGGAG
CGCACCACAGCGGCGTTGGAGCTGCCCTGGCTGGCCTTGACATGTCGATG
```

-continued

```
CCAGGAGACACCGCCTTTGGTACCGGCAAATCCTTCTGGGGAACCAACCT

GACCATCGCCGTTCTCAACGGCACTGTTCCGGAATGGCGTGTGGATGACA

TGGCTGTTCGCATCATGGCGGCCTTTTACAAGGTTGGTCGCGACCGTTAC

CAGGTGCCGGTCAACTTCGACTCGTGGACGAAGGATGAATACGGTTACGA

GCACGCACTGGTTGGCCAGAACTATGTCAAGGTCAATGACAAGGTGGATG

TTCGTGCCGACCATGCGGACATCATCCGTCAAATTGGGTCTGCTAGTGTT

GTCCTTCTTAAGAACGATGGAGGACTCCCATTGACCGGCTATGAAAAGTT

CACCGGAGTTTTTGGAGAGGATGCCGGATCGAACCGTTGGGCGCTGACG

GCTGCTCTGATCGTGGTTGCGACAACGGCACGTTGGCAATGGGTTGGGGC

AGTGGCACTGCTGACTTCCCCTACCTTGTCACTCCCGAGCAGGCAATCCA

GAATGAAATCCTTTCCAAGGGGAAGGGGTTAGTGAGTGCTGTCACCGACA

ATGGTGCCCTGGACCAGATGGAACAGGTTGCGTCTCAGGCCAGCGTTTCT

ATCGTTTTCGTCAACGCCGACTCTGGTGAAGGCTACATCAACGTTGATGG

CAACGAAGGTGATCGGAAGAACCTCACCCTCTGGAAGGGAGGCGAGGAGG

TGATCAAGACTGTTGCAGCCAACTGCAACAACACCATTGTTGTGATGCAC

ACTGTGGGACCTGTCTTGATCGATGAGTGGTATGACAACCCCAACGTCAC

CGCCATCGTCTGGGCCGGTCTTCCAGGCCAGGAGAGCGGCAACAGTCTCG

TCGATGTGCTCTACGGCCGTGTCAGCCCCGGAGGAAAGACGCCGTTTACG

TGGGGAAAGACTCGCGAGTCGTACGGCGCTCCTCTGCTCACCAAACCCAA

CAACGGCAAGGGTGCCCCCCAGGACGACTTCACCGAGGGCGTCTTCATCG

ACTACAGAAGGTTCGACAAGTACAACGAGACGCCCATCTATGAGTTCGGG

TTTGGTCTGAGTTATACCACTTTTGAATACTCGGACATCTACGTCCAGCC

CCTTAACGCACGACCTTACACCCCAGCCTCCGGCAGCACCAAGGCGGCTC

CTACCTTTGGGAACATCAGCACGGACTATGCAGATTACTTGTACCCTGAG

GATATACACAAGGTCCCATTATACATCTATCCTTGGCTTAACACGACGGA

CCCGAAGAAGTCCTCCGGCGATCCCGACTACGGAATGAAGGCCGAGGACT

ACATCCCATCTGGCGCGACTGATGGATCTCCTCAGCCCATCCTTCCGGCA

GGCGGTGCTCCTGGTGGCAACCCGGGTCTCTATGATGAGATGTACAGGGT

ATCTGCAATCATCACCAACACCGGTAACGTTGTTGGTGATGAGGTTCCTC

AGCTGTATGTCTCTCTTGGTGGTCCAGATGACCCCAAGGTCGTGCTCCGC

AACTTTGACCGCATCACGCTCCACCCCGGCCAGCAGACAATGTGGACCAC

GACATTGACGCGACGCGATATCTCGAACTGGGACCCTGCCTCCCAGAATT

GGGTTGTGACCAAATATCCCAAGACAGTCTACATCGGCAGCTCTTCGCGG

AAACTGCACCTGCAGGCACCGCTTCCCCCTTAC
```

The polypeptide sequence of the *T. aurantiacus* β-glucosidase pre-protein is shown below:

```
                                        (SEQ ID NO: 6)
MRLGWLELAVAAAATVASAKDDLAYSPPFYPSPWMDGNGEWAEAYRRAVD

FVSQLTLAEKVNLTTGVGWMQEKCVGETGSIPRLGFRGLCLQDSPLGVRF

ADYVSAFPAGVNVAATWDKNLAYLRGKAMGEEHRGKGVDVQLGPVAGPLG

RHPDGGRNWEGFSPDPVLTGVLMAETIKGIQDAGVIACAKHFIGNEMEHF

RQASEAVGYGFDITESVSSNIDDKTLHELYLWPFADAVRAGVGSFMCSYN

QVNNSYSCSNSYLLNKLLKSELDFQGFVMSDWGAHHSGVGAALAGLDMSM

PGDTAFGTGKSFWGTNLTIAVLNGTVPEWRVDDMAVRIMAAFYKVGRDRY

QVPVNFDSWTKDEYGYEHALVGQNYVKVNDKVDVRADHADIIRQIGSASV

VLLKNDGGLPLTGYEKFTGVFGEDAGSNRWGADGCSDRGCDNGTLAMGWG

SGTADFPYLVTPEQAIQNEILSKGKGLVSAVTDNGALDQMEQVASQASVS

IVFVNADSGEGYINVDGNEGDRKNLTLWKGGEEVIKTVAANCNNTIVVMH

TVGPVLIDEWYDNPNVTAIVWAGLPGQESGNSLVDVLYGRVSPGGKTPFT

WGKTRESYGAPLLTKPNNGKGAPQDDFTEGVFIDYRRFDKYNETPIYEFG

FGLSYTTFEYSDIYVQPLNARPYTPASGSTKAAPTFGNISTDYADYLYPE

DIHKVPLYIYPWLNTTDPKKSSGDPDYGMKAEDYIPSGATDGSPQPILPA

GGAPGGNPGLYDEMYRVSAIITNTGNVVGDEVPQLYVSLGGPDDPKVVLR

NFDRITLHPGQQTMWTTTLTRRDISNWDPASQNWVVTKYPKTVYIGSSSR

KLHLQAPLPPY
```

The polynucleotide sequence encoding WT$^M$ designed with codon biasing for expression in *Saccharomyces cerevisiae* is shown below:

```
                                        (SEQ ID NO: 7)
TGAAAGATGATTTGGCTTATAGTCCACCTTTCTACCCATCACCTTGGATG

GACGGTAACGGAGAATGGGCTGAAGCCTATAGAAGAGCCGTCGATTTCGT

ATCCCAATTGACATTGGCAGAGAAGGTAAATTTGACAACCGGAGTGGGTT

GGATGCAGGAAAAGTGTGTAGGCGAAACTGGTTCTATACCAAGATTAGGC

TTTAGGGGTTTGTGCTTACAAGATTCTCCCTTAGGTGTAAGATTCGCCGA

CTACGTAAGTGCTTTTCCTGCAGGAGTTAACGTTGCAGCAACTTGGGATA

AAAACCTTGCATATTTGAGAGGTAAGGCAATGGGTGAAGAACATCGTGGC

AAGGGTGTCGATGTGCAGTTAGGCCCAGTTGCTGGACCATTGGGAAGACA

TCCCGACGGCGGAAGAAACTGGGAGGGTTTTAGTCCAGACCCCGTTTTGA

CTGGAGTCTTGATGGCAGAGACTATCAAAGGTATACAAGACGCTGGAGTG

ATTGCTTGTGCTAAACATTTCATTGGTAACGAAATGGAACATTTCAGACA

AGCCTCCGAAGCAGTTGGCTATGGTTTTGATATTACTGAGTCCGTTTCAT

CAAACATAGATGACAAAACCCTTCACGAACTATATTTATGGCCATTCGCT

GATGCCGTCAGAGCTGGTGTAGGTTCTTTCATGTGTTCATACAACCAAGT

CAACAACTCTTATTCATGCTCTAATTCCTACTTGTTGAACAAATTATTAA

AGTCAGAACTTGACTTTCAAGGTTTCGTAATGTCCGACTGGGGTGCTCAC

CATTCCGGAGTTGGTGCAGCTTTGGCCGGTTTAGACATGTCAATGCCAGG

TGATACTGCATTTGGAACGGGTAAATCCTTTTGGGGTACCAATCTAACCA

TCGCCGTCCTTAATGGTACAGTTCCTGAATGGAGAGTAGATGATATGGCT

GTTAGAATCATGGCCGCATTTTACAAAGTTGGTAGAGATAGGTACCAAGT

GCCTGTCAACTTTGACTCCTGGACCAAAGATGAATATGGTTATGAACACG

CATTGGTGGGCCAGAATTATGTTAAGGTCAATGATAAAGTGGATGTGAGA
```

-continued

```
GCTGACCACGCTGATATTATCCGTCAGATTGGTAGTGCATCAGTTGTTTT

GTTAAAAAATGACGGAGGACTTCCTTTAACTGGTTATGAGAAGTTCACAG

GCGTATTCGGCGAAGATGCCGGTAGTAATCGTTGGGGTGCTGACGGATGC

AGTGACAGAGGCTGCGATAATGGTACCCTTGCCATGGGTTGGGGATCTGG

AACGGCCGACTTTCCTTACTTAGTTACGCCAGAGCAGGCTATACAAAATG

AGATTTTGTCTAAAGGCAAGGGACTTGTCTCTGCCGTGACGGATAACGGA

GCTTTAGACCAAATGGAACAGGTCGCTTCCCAAGCTTCTGTAAGTATTGT

TTTTGTTAATGCCGACTCAGGAGAAGGCTATATTAACGTTGATGGAAATG

AAGGTGATAGGAAAAATCTAACTCTTTGGAAGGGTGGTGAAGAGGTCATT

AAGACAGTCGCAGCCAATTGTAACAATACCATCGTCGTAATGCACACCGT

TGGACCTGTGTTAATAGATGAATGGTATGATAATCCTAATGTCACTGCAA

TTGTTTGGGCAGGCTTGCCTGGTCAGGAATCCGGTAATTCTCTTGTTGAT

GTCCTATATGGAAGGGTGTCCCCTGGTGGAAAAACTCCCTTTACTTGGGG

CAAGACACGTGAAAGTTATGGAGCACCATTATTAACAAAACCAAACAACG

GAAAGGGAGCTCCTCAAGATGATTTTACAGAGGGTGTTTTCATCGACTAC

AGGCGTTTCGACAAGTATAACGAGACTCCTATATATGAGTTCGGATTTGG

TCTATCCTACACAACTTTTGAGTACTCAGATATCTACGTACAGCCCTTGA

ACGCACGTCCATACACCCCTGCTTCAGGTTCTACTAAGGCCGCCCCAACG

TTTGGAAATATATCTACTGATTACGCTGATTACCTATACCCAGAGGATAT

TCATAAAGTTCCACTTTATATCTACCCATGGCTTAATACGACAGACCCAA

AAAAGTCAAGTGGTGATCCAGATTACGGAATGAAAGCTGAAGATTACATT

CCTTCAGGCGCTACGGACGGCTCTCCCCAACCAATTCTACCAGCTGGAGG

TGCTCCAGGTGGTAATCCTGGCTTGTATGATGAGATGTATAGGGTTTCTG

CTATAATTACAAATACAGGTAACGTTGTTGGTGATGAGGTACCTCAACTA

TACGTGTCTTTAGGTGGTCCCGATGACCCCAAGGTAGTTTTGCGTAACTT

TGACAGAATCACTTTGCATCCAGGACAACAAACCATGTGGACTACGACTT

TGACAAGAAGAGATATATCTAATTGGGACCCTGCATCTCAGAATTGGGTT

GTGACAAAGTACCCAAAAACTGTCTATATCGGCTCAAGTTCCAGGAAGCT

TCACTTGCAGGCCCCTCTACCCCCATACTAA
```

The fungus Thermoascus aurantiacus produces a variety of enzymes that act in concert to catalyze decrystallization and hydrolysis of cellulose to yield soluble sugars. Among these is the *T. aurantiacus* β-glucosidase 1 (Bgl1) (Parry et al., Biochem. J. 353:117 [2001], incorporated herein by reference). The *T. aurantiacus* β-glucosidase protein sequence is provided in Hong et al., Appl. Microbiol. Biotechnol., 73:1331 [2007], incorporated herein by reference. The sequence of the bgl1 gene was reported by Hong et al. (Hong et al. NCBI accession DQ114396.1; Genbank Accession AAZ95588). The *T. aurantiacus* wild-type β-glucosidase cDNA sequence is provided as GenBank Accession No. DQ114397 (See also, Hong et al., J. Biotechnol., 130:114-23 [2007]) and is set forth herein as SEQ ID NO:6 herein. The *T. aurantiacus* β-glucosidase pre-protein (SEQ ID NO:6) includes a 19-residue signal peptide, MRLGWLELA-VAAAATVASA, corresponding to residues 1-19 of SEQ ID NO:6 (the polynucleotide encoding this pre-protein is provided in SEQ ID NO:5).

The *T. aurantiacus* β-glucosidase variants described herein are particularly useful for production of fermentable sugars from cellulosic biomass. In some embodiments, the present invention provides methods of producing glucose by contacting a composition comprising cellobiose with at least one recombinantly expressed *T. aurantiacus* β-glucosidase variant under conditions in which the cellobiose is enzymatically converted to glucose. In some embodiments, recombinant host cells expressing at least one β-glucosidase variant are combined with cellobiose under conditions in which the β-glucosidase is expressed (and preferably secreted) by the cells. In some alternate embodiments, purified or partially purified recombinant β-glucosidase enzyme is contacted with cellobiose. In some embodiments of the present invention, contacting comprises culturing a recombinant host cell in a medium that contains cellobiose produced from a cellulosic feedstock. For example, the *T. aurantiacus* β-glucosidase variants described herein demonstrate benefit in saccharification reactions in conjunction with other cellulases, such as *T. reesei* cellulases (e.g., *T. reesei* CBH1, CBH2, and/or EG1 or variants thereof, and/or *T. reesei* broth) and *C. lucknowense* cellulases (See, U.S. Pat. Nos. 6,015,707, 5,811,381 and 6,573,086; US Pat. Pub. Nos. 2007/0238155, 2008/0194005, 2009/0099079; and WO 2008/073914 and WO 98/15633, all of which are incorporated by reference).

In some embodiments, the present invention provides methods for expressing β-glucosidase enzymes by culturing a host cell comprising a vector comprising a nucleic acid sequence encoding *T. aurantiacus* Bgl1 variant under conditions in which the β-glucosidase protein or an enzymatically active fragment thereof is expressed. In some embodiments, the expressed protein comprises a signal peptide which is removed by the cell as the enzyme is secreted. In some embodiments, transcription of the sequence encoding the *T. aurantiacus* Bgl1 variant is controlled by an operably linked heterologous promoter.

β-Glucosidase Polypeptide Variants

The present invention provides novel enzymes that are *T. aurantiacus* β-glucosidase (Bgl1) variants. β-glucosidase polypeptide variants of the present invention are variants of Bgl1 that exhibit β-glucosidase activity, typically greater β-glucosidase activity than the wild-type *T. aurantiacus* β-glucosidase (SEQ ID NO:2) or $WT^M$ *T. aurantiacus* β-glucosidase (SEQ ID NO:4). Also included are β-glucosidase polypeptide variants that exhibit greater stability under conditions relevant to commercial saccharification processes.

The present invention provides Bgl1 variants having greater activity than wild-type *T. aurantiacus* Bgl1 protein and having at least one of the substitutions found in a variant that exhibits increased activity described herein. As is discussed in more detail herein, a polynucleotide encoding the wild-type (WT) *T. aurantiacus* Bgl1 protein (SEQ ID NO:2) or a wild-type *T. aurantiacus* Bgl1 protein modified by addition of methionine at the amino terminus of the mature protein ($WT^M$; SEQ ID NO:4) was prepared. The polynucleotide, along with a sequence encoding a heterologous signal peptide, was inserted into an expression vector, as described in the Examples. Libraries of polynucleotides encoding variant Bgl1 proteins were prepared by mutagenesis and directed evolution, and the properties (e.g., β-glucosidase activity) of individual Bgl1 variants were assessed, as described in the Examples. A number of amino acid substitutions and combinations of substitutions were identified in variants with activity greater than the wild-type enzyme's activity. It is also intended that the present invention encompass Bgl1 variants comprising at least one insertion and/or deletion, as compared to a reference sequence (e.g., SEQ ID NO:2 or 4).

More specifically, the present invention provides isolated and/or recombinant β-glucosidase polypeptide variants with increased activity comprising amino acid sequences that are at least about 70% identical to wildtype *T. aurantiacus* β-glucosidase (Bgl1) (SEQ ID NO:2) and that have at least one substitution of an amino acid residue at a position selected from A478, D203, E344, F287, H684, K100, K291, K342, K456, K54, L149, N355, N650, P739, P790, R330, S408, S86, T150, Y331, Y641, Y679, Y746 (wherein amino acid position is determined by optimal alignment with SEQ ID NO:2). The present invention also provides isolated and/or recombinant β-glucosidase polypeptide variants comprising amino acid sequences that are at least about 70% identical to WT$^M$ *T. aurantiacus* β-glucosidase (Bgl1) (SEQ ID NO:4) and that have at least one substitution or deletion of an amino acid residue at a position selected from A479, D204, E345, F288, H685, K101, K292, K343, K457, K55, L150, M1, N356, N651, P740, P791, R331, S409, S87, T151, Y332, Y642, Y680, and Y747 (wherein the amino acid position is determined by optimal alignment with SEQ ID NO:4). "Substitution," in this context, means that the residue in the variant protein is any residue other than the residue at that position in the reference sequence (e.g., SEQ ID NO:2 or 4). For example, "A479X" denotes a variant comprising an amino acid other than alanine at position 479 (i.e., one of the other 19 naturally occurring amino acids). In some embodiments, the amino acid in the variant protein is neither the wild-type residue nor a residue that is a conservative substitute for the wild-type residue. As indicated below, in this context, a conservative substitute for a residue is another residue in the same group (i.e., a basic amino acid, such as arginine, lysine or histidine; an acidic amino acid, such as glutamic acid or aspartic acid; a polar amino acid, such as glutamine or asparagines; a hydrophobic amino acid, such as leucine, isoleucine, or valine; an aromatic amino acid, such as phenylalanine, tryptophan, or tyrosine; or a small amino acid, such as glycine, alanine, serine, threonine, proline, cysteine, or methionine.

In some embodiments, the amino acid in the variant protein is neither the wild-type residue nor a residue that is a residue commonly exchanged with the wild-type residue as defined by the following pairs: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In some embodiments, the present invention provides isolated and/or recombinant β-glucosidase polypeptide variants having greater activity and/or thermostability than the wild-type (WT) *T. aurantiacus* Bgl1 protein, and comprise amino acid sequences that are at least about 70% identical to wild-type *T. aurantiacus* β-glucosidase (Bgl1) (SEQ ID NO:2) and have at least one substitution of an amino acid residue selected from A478V, D203G, E344V, F287Y, H684Y, K100R, K291E, K291I, K342R, K456R, K54R, L149V, N355S, N650K, P739S, P790T, R330K, S408N, S86N, T150S, Y331C, Y641N, Y679F, Y746C (wherein the amino acid position is determined by optimal alignment with SEQ ID NO:2). Beneficial combinations of the above-listed inventions include any combination of substitutions at any 2, 3, 4, 5, 6, 7, 8, 9, 10, 11, 12, 13, 14, 15, 16, 17, 18, 19, 20, 21, 22, 23, or 24, or more of the above-identified positions.

The present invention also provides isolated and/or recombinant β-glucosidase polypeptide variants having greater activity and/or thermostability than the wild-type (WT) *T. aurantiacus* Bgl1 protein and comprise amino acid sequences that are at least about 70% identical to WT$^M$ *T. aurantiacus* β-glucosidase (Bgl1) (SEQ ID NO:4) and that has at least one substitution of an amino acid residue at a position selected from A479V, D204G, E345V, F288Y, H685Y, K101R, K292E, K292I, K343R, K457R, K55R, L150V, M1T, N356S, N651K, P740S, P791T, R331K, S409N, S87N, T151S, Y332C, Y642N, Y680F, and Y747C (wherein the amino acid position is determined by optimal alignment with SEQ ID NO:4). Beneficial combinations of the above-listed inventions include any combination of substitutions at any 2, 3, 4, 5, 6, 7, 8, 9, 10, 11, 12, 13, 14, 15, 16, 17, 18, 19, 20, 21, 22, 23, or 24, or more of the above-identified positions.

In some embodiments, the present invention provides isolated and/or recombinant β-glucosidase polypeptide variants having amino acid sequences encoded by nucleic acids that hybridize under stringent conditions to the complement of SEQ ID NO:1 (e.g., over substantially the entire length of a nucleic acid exactly complementary to SEQ ID NO:1) wherein the encoded polypeptides have at least one or more substitutions or deletions at a position selected from A478, D203, E344, F287, H684, K100, K291, K342, K456, K54, L149, N355, N650, P739, P790, R330, S408, S86, T150, Y331, Y641, Y679, Y746 (wherein the amino acid position is determined by optimal alignment with SEQ ID NO:2). The present invention also provides isolated and/or recombinant β-glucosidase polypeptide variants having amino acid sequences encoded by nucleic acids that hybridize under stringent conditions to the complement of SEQ ID NO:1 (e.g., over substantially the entire length of a nucleic acid exactly complementary to SEQ ID NO:1) wherein the encoded polypeptides have at least one or more substitutions or deletions at a position selected from A479, D204, E345, F288, H685, K101, K292, K343, K457, K55, L150, M1, N356, N651, P740, P791, R331, S409, S87, T151, Y332, Y642, Y680, and Y747 (wherein the amino acid position is determined by optimal alignment with SEQ ID NO:4).

The present invention further provides isolated and/or recombinant β-glucosidase polypeptide variants having amino acid sequences encoded by nucleic acids that hybridize under stringent conditions to the complement of SEQ ID NO:1 (e.g., over substantially the entire length of a nucleic acid exactly complementary to SEQ ID NO:1) wherein the encoded polypeptides have at least one or more substitutions or deletions at a position selected from A478V, D203G, E344V, F287Y, H684Y, K100R, K291E, K291I, K342R, K456R, K54R, L149V, N355S, N650K, P739S, P790T, R330K, S408N, S86N, T150S, Y331C, Y641N, Y679F, Y746C and Y747C (wherein the amino acid position is determined by optimal alignment with SEQ ID NO:2) or which have at least one substitution or deletion of an amino acid residue at a position selected from A479V, D204G, E345V, F288Y, H685Y, K101R, K292E, K292I, K343R, K457R, K55R, L150V, M1T, N356S, N651K, P740S, P791T, R331K, S409N, S87N, T151S, Y332C, Y642N, Y680F (wherein the amino acid position is determined by optimal alignment with SEQ ID NO:4). Beneficial combinations of the above-listed inventions include any combination of substitutions at any 2, 3, 4, 5, 6, 7, 8, 9, 10, 11, 12, 13, 14, 15, 16, 17, 18, 19, 20, 21, 22, 23, or 24, or more of the above-identified positions.

It is intended that the Bgl1 variants provided herein encompass additional amino acid substitutions beyond those listed above (e.g., additional conservative substitutions) and may be less-than-full length compared to wild-type *T. aurantiacus* Bgl1 protein. Thus, in some embodiments, the Bgl1 variants of the present invention comprise insertions and/or deletions (e.g., truncation at the amino- and/or carboxy-termini) relative to SEQ ID NO:2. The wild-type secreted form of *T. aurantiacus* Bgl1 protein is about 842 residues in length; variants of the present invention may be longer or shorter than the wild-type protein. For illustration and not limitation, in some embodiments the variant may be longer or shorter by up to about 10% of the wild-type length, up to about 5%, up to about 4%, up to about 3%, up to about 2%, or about up to 1%.

Sequence-activity analyses of variants were performed in accordance with methods known in the art (See, WO 03/075129 and U.S. patent application Ser. No. 10/379,378, as well as Fox et al., Protein Eng., 16(8):589-597 [2003]; and Fox et al., J. Theor. Biol. 234(2):187-199 [2005], all of which are incorporated herein by reference), to identify substitutions likely to provide the most significant effects on activity. Some β-glucosidase variants of the present invention have amino acid sequences that include at least one substitution of an amino acid residue at either or both positions 287 and 86 (e.g., F287Y and S86N). Some β-glucosidase variants of the present invention have an amino acid sequence that includes at least one substitution of an amino acid residue at a position selected from H684Y, K342R, P790T, S408N, T150S and Y641N, which appear to be very beneficial substitutions. Some β-glucosidase variants of the present invention have amino acid sequences that include at least one substitution of an amino acid residue at a position selected from A478V, D203G, E344V, K291E, K291I, K456R, K54R, L149V, P739S, Y679F, and Y746C. In addition, some variants comprise a sequence having the addition of a threonine residue at the amino terminus of SEQ ID NO:2. It will be recognized that the aforementioned beneficial substitutions are referred to using the numbering of SEQ ID NO:2. Using the numbering of SEQ ID NO:4, highly beneficial substitutions include F288Y and S87N, very beneficial substitutions include H685Y, K343R, P791T, S409N, T151S, and Y642N, and additional beneficial substitutions include A479V, D204G, E345V, K292E, K292I, K457R, K55R, L150V, M1T, P740S, Y680F, and Y747C. Suitable combinations include any combination of substitutions at any 2, 3, 4, 5, 6, 7, 8, 9, 10, 11, 12, 13, 14, 15, 16, 17 or 18, or more of the above-identified positions. In some embodiments, the β-glucosidase variants of the present invention further have an amino acid sequence wherein no substitution is made at a position corresponding to N356 (using the numbering of SEQ ID NO:2).

In some embodiments, the isolated and/or recombinant β-glucosidase polypeptide variant of the present invention is at least about 70% identical to WT *T. aurantiacus* Bgl1 or WT$^M$ Bgl1, and comprises a substitution set selected from: T150S+Y641N+N650K; K100R+T150S+K291E+K342R+ S408N+Y641N+P739S; T150S+K342R+S408N+A478V+ Y641N+Y679F; L149V+T150S+K342R+S408N+K456R+ Y641N+N650K; S86N+T150S+F287Y+Y641N+N650K; K100R+T150S+K342R+N355S+S408N+Y641N+N650K; S86N+T150S+F287Y+Y641N+N650K; K54R+K100R+ T150S+R330K+Y331C+K342R+N355S+S408N+Y641N; D203G+K291I+E344V+Y746C; and H684Y+P790T (where amino acid position is determined by optimal alignment with SEQ ID NO:2), or T151S+Y642N+N651K; M1T+K101R+ T151S+K292E+K343R+S409N+Y642N+P740S; M1T+ T151S+K343R+S409N+A479V+Y642N+Y680F; L150V+ T151S+K343R+S409N+K457R+Y642N+N651K; S87N+ T151S+F288Y+Y642N+N651K; K101R+T151S+K343R+ N356S+S409N+Y642N+N651K; M1T+K55R+K101R+ T151S+R331K+Y332C+K343R+N356S+S409N+Y642N; K101R+T151S+K343R+N356S+S409N+Y642N+N651K; D204G+K292I+E345V+Y747C; and H685Y+P791T (where amino acid position is determined by optimal alignment with SEQ ID NO:4).

As noted above, β-glucosidase polypeptides encompassed by the invention have at least about 70% sequence identity to SEQ ID NO:2 or to SEQ ID NO:4. In some embodiments, β-glucosidase polypeptides encompassed by the invention include those having an amino acid sequence at least about 71% identical, at least about 72% identical, at least about 73% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical or at least about 99% identical to SEQ ID NO:2 or to SEQ ID NO:4.

Each recitation herein of "at least about 70%" should be understood to also include, in the alternative, any of the higher values above.

As noted above, in some embodiments, Bgl1 variants of the present invention encompass additional amino acid substitutions beyond those listed above including, for example, variants with one or more additional conservative substitutions made in their amino acid sequences. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine, proline, cysteine and methionine) Amino acid substitutions that do not generally alter the specific activity are known in the art. The most commonly occurring exchanges include, but are not limited to Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, as well as these pairs in reverse.

Conservatively substituted variations of the β-glucosidase polypeptide variants of the present invention include substitutions of a small percentage, typically less than about 5%, more typically less than about 2%, and often less than about 1% of the amino acids of the polypeptide sequence, with a conservatively selected amino acid of the same conservative substitution group. The addition of sequences that do not alter the encoded activity of a β-glucosidase, such as the addition of a non-functional or non-coding sequence, are considered to be conservative variations of the β-glucosidase polynucleotide.

The present invention also provides enzymatically active fragments of the β-glucosidase polypeptide variants described herein, wherein the fragments have β-glucosidase activity and at least one substitution described herein. The present invention further encompasses β-glucosidases variants comprising truncated amino and/or carboxy termini. Accordingly, the present invention further provides isolated and/or recombinant β-glucosidase polypeptide variants having amino acid sequences having a deletion of from about 1 to about 50 amino acid residues from the carboxy (C-) terminus, the amino (N-) terminus, or both (i.e., a deletion of 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acid residues from either or both the N- or C-terminus) with respect to SEQ ID NO:2 or 4. In some embodiments, the deletion is from about 1 to about 15 amino acid residues from the N-terminus and/or from about 1 to about 40 amino acid residues from the C-terminus. These β-glucosidase fragments are also referred to herein as "N-terminally truncated" and "C-terminally truncated" β-glucosidase polypeptide variants, respectively. In some embodiments, the deletion is from about 1 to about 30, or about 1 to about 20, or about 1 to about 10 residues, or about 1 to about 5 residues from the C-terminus, the N-terminus, or both termini.

Some β-glucosidase variants of the invention having at least about 70% sequence identity to SEQ ID NO:2 and one or more substitutions disclosed herein, also have one or more substitutions, deletions or insertions in addition to those specifically set forth herein. The effect, if any, of such substitutions, deletions or insertions on β-glucosidase activity and thermostability can be determined using any suitable assay known in the art. For illustration, TaB2 has the following substitutions T151S+Y642N+N651K, relative to SEQ ID NO:2. To determine the effect of a further substitution (e.g., replacement of leucine at position 4 of SEQ ID NO:2 with valine) the variant (in this case, SEQ ID NO:2, with L4V+ T151S+Y642N+N651K) is expressed and its properties compared to the parent (in this case, TaB2).

In some embodiments, libraries of β-glucosidase polypeptide variants (and polynucleotides encoding the variants) are generated and screened (e.g., using high throughput screening) for presence of β-glucosidase activity. In some embodiments, mutagenesis and directed evolution methods known in the art are applied to polynucleotides encoding β-glucosidase variants exemplified herein to generate variant libraries that are expressed, screened, and assayed using any suitable methods, including those described herein. Mutagenesis and directed evolution methods are well known in the art (See e.g., Ling, et al., Anal. Biochem., 254:157-78 [1999]; Dale et al., Methods Mol. Biol., 57:369-74 [1996]; Smith, Ann. Rev. Genet., 19:423-462 [1985]; Botstein et al., Science, 229: 1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri et al., Nat. Biotechnol., 15:436-438 [1997]; Zhang et al., Proc. Nat. Acad. Sci., U.S.A., 94:45-4-4509 [1997]; Crameri et al., Nat. Biotechnol., 14:315-319 [1996]; Stemmer, Nature, 370:389-391 [1994]; Stemmer, Proc. Nat. Acad. Sci., U.S.A., 91:10747-10751 [1994]; WO 95/22625; WO 97/0078; WO 97/35966; WO 98/27230; WO 00/42651; and WO 01/75767, all of which are incorporated herein by reference).

In generating variants that comprise substitutions, insertions or deletions at positions in addition to those described supra, the ordinarily skilled practitioner will be aware that certain regions of the β-glucosidase protein are less tolerant than others to substitutions (especially non-conservative substitutions). Thus, in some embodiments, variant Bgl1 proteins retain conserved residues and functional domains from the parent. For example, alignments of several glycosyl hydrolase family 3 (GH3 type) enzymes including T. aurantiacus β-glucosidase 1, find use in determining sites for modification. In some of these alignments, the GH3 active site, catalytic residues and residues that are conserved (similar) or highly conserved (identical) in the family are identified (See e.g., Bhatia et al., Crit. Rev Biotechnol., 22: 375-407 [2002]; and Hong et al., supra; both of which are incorporated herein by reference). In some embodiments of the present invention, the variant proteins retain some or all of these residues or classes of residues from the parent (i.e., there are no substitutions of some or all of the conserved positions).

TABLE 1

Conserved Residues in T. aurantiacus β-Glucosidase 1

Amino Acid Position in SEQ ID NO: 2

| | |
|---|---|
| Identical Residues | S35; T46; R65; D75; G79; F89; P90; A97; T98; D100; L103; G108; A110; E114; G119; P126; R133; P135; G138; R139; E142; D147; I159; G161; Q163; N202; G223; M228; Y231; N235; N242; L250; K251; L254; F256; G258; F259; V260; D263; W264; A274; D285; L299; V303; G306; P309; R312; D315; R319; I320; G328; G347; H370; L384; L385; K386; N387; A407; G421; G425; W431; T435; T443; A447; V484; E492; G502; D503; L507; V529; L556; P557; G558; E560; G562; D567; L569; G571; P580; T582 |
| Similar Residues | V34; K42; L71; S87; V93; V95; A96; G112; G125; G129; L131; W141; F144; L150; I162; F174; I175; I195; L208; L211; L213; F216; A219; V220; L246; M261; S262; M282; G284; W295; T297; T300; V308; V313; M321; Y325; I373; R375; G378; G413; M429; I448; A476; G513; I517; V530; M531; P536; V537; L538; I539; I551; V552; A554; L565; Y570; K578; K585; E588; Y617 |
| Conserved Regions | 248-265; 489-495 |

Signal Peptide

In some embodiments, the β-glucosidase polypeptides are secreted from the host cell in which they are expressed (e.g., a yeast or other fungal cell) and are expressed as a pre-protein including a signal peptide (i.e., an amino acid sequence linked to the amino terminus of a polypeptide and which directs the encoded polypeptide into the cell secretory pathway). In some embodiments, the signal peptide is the endogenous T. aurantiacus β-glucosidase signal peptide having the sequence set forth as residues 1-19 of SEQ ID NO:6. In some other embodiments, signal peptides from other T. aurantiacus secreted proteins are used.

In some additional embodiments, other signal peptides find use, depending on the host cell and other factors. Effective signal peptide coding regions for filamentous fungal host cells include, but are not limited to, the signal peptide coding regions obtained from Aspergillus oryzae TAKA amylase, Aspergillus niger neutral amylase, A. niger glucoamylase, Rhizomucor miehei aspartic proteinase, Humicola insolens cellulase, Humicola lanuginosa lipase, and T. reesei cellobiohydrolase II (TrCBH2).

Effective signal peptide coding regions for bacterial host cells include, but are not limited to, the signal peptide coding regions obtained from the genes for Bacillus NC1B 11837 maltogenic amylase, Bacillus stearothermophilus alpha-amylase, Bacillus licheniformis subtilisin, B. licheniformis β-lactamase, B. stearothermophilus neutral proteases (nprT, nprS, nprM), and Bacillus subtilis prsA. Additional signal peptides are known in the art (See e.g., Simonen and Palva, Microbiol. Rev., 57: 109-137 [1993], incorporated herein by reference).

Useful signal peptides for yeast host cells also include those from the genes for Saccharomyces cerevisiae alpha-factor, S. cerevisiae SUC2 invertase (See e.g., Taussig and Carlson, Nucl. Acids Res., 11:1943-54 [1983]; and SwissProt Accession No. P00724), and others (See e.g., Romanos et al., Yeast 8:423-488 [1992], which is incorporated herein by reference). Suitable variants of these signal peptides and other signal peptides also find use in the present invention.

Fusion Polypeptides and Additional Sequence Elements

In some embodiments, the β-glucosidase polypeptide variants of the present invention include additional sequences which do not alter the encoded activity of the β-glucosidases. For example, in some embodiments, the β-glucosidase is linked to an epitope tag or to other sequence useful in β-glucosidase purification.

The present invention also provides β-glucosidase variant fusion polypeptides. In some embodiments, the fusion polypeptide comprises an amino acid sequence encoding a β-glucosidase variant polypeptide of the present invention or a fragment thereof, linked either directly or indirectly through the N- or C-terminus of the β-glucosidase variant polypeptide to an amino acid sequence encoding at least a second (additional) polypeptide. In some embodiments, the β-glucosidase variant fusion polypeptides further include amino acid sequences encoding a third, fourth, fifth, or additional polypeptides. Typically, each additional polypeptide has a biological activity, or alternatively, is a portion of a polypeptide that has a biological activity, where the portion has the effect of improving expression and/or secretion of the fusion polypeptide from the desired expression host. In some embodiments, these sequences are fused, either directly or indirectly, to the N- or C-terminus of the β-glucosidase variant polypeptide or fragment thereof, or alternatively, to the N- or C-terminus of the additional polypeptides having biological activity.

In some embodiments, the additional polypeptide(s) encode an enzyme or active fragment thereof, and/or a polypeptide that improves expression and/or secretion of the fusion polypeptide from the desired expression host cell. In some other embodiments, the additional polypeptide(s) encode(s) a cellulase (e.g., a β-glucosidase having a different amino acid sequence from the β-glucosidase variant polypeptide in the fusion polypeptide, for example, a wildtype β-glucosidase or a variant thereof, including a different T. aurentiacus β-glucosidase variant polypeptide), or a polypeptide exhibiting CBH or EG activity), and/or a polypeptide that improves expression and secretion from the desired host cell (e.g., a polypeptide that is normally expressed and secreted from the desired expression host, such as a secreted polypeptide normally expressed from filamentous fungi). These include, but are not limited to glucoamylase, α-amylase and aspartyl proteases from Aspergillus niger, A. niger var. awamori, Aspergillus oryzae, cellobiohydrolase I, and cellobiohydrolase II, Trichoderma endoglucanase I and endoglucase III, and Neurospora and Humicola glucoamylases (See e.g., WO 98/31821, which is incorporated herein by reference).

In some embodiments, the polypeptide components of the fusion polypeptide are linked to each other indirectly via a linker. Linkers suitable for use in the practice of the present invention include, but are not limited to those described in WO 2007/075899, which is incorporated herein by reference. Exemplary linkers include peptide linkers of from about 1 to about 40 amino acid residues in length, including those from about 1 to about 20 amino acid residues in length, and those from about 1 to about 10 amino acid residues in length. In some embodiments, the linkers are made up of a single amino acid residue, such as, for example, a Gly, Ser, Ala, or Thr residue, or combinations thereof, particularly Gly and Ser. In some embodiments, the linkers employed in the practice of the present invention are cleavable. In some embodiments, suitable cleavable linkers contain a cleavage site, such as a protease recognition site. Exemplary protease recognition sites are well known in the art and include, but are not limited to Lys-Arg (e.g., the KEX2 protease recognition site, which can be cleaved by a native Aspergillus KEX2-like protease), and Lys and Arg (e.g., the trypsin protease recognition sites) (See e.g., WO 07/075,899, which is incorporated herein by reference).

β-Glucosidase Activity

β-glucosidase polypeptide variants of the present invention include those having improved (e.g., greater) β-glucosidase activity relative to wildtype T. aurantiacus β-glucosidase (SEQ ID NO:2) under specified conditions. Improved β-glucosidase activity may be measured as described herein. In some embodiments, the β-glucosidase polypeptides of the present invention have β-glucosidase activity levels that are at least about 1-fold, at least about 2-fold, at least about 2.5-fold, at least about 2.7-fold, or more than 2.7-fold greater than wildtype T. aurantiacus β-glucosidase (SEQ ID NO:2) when assayed under the same conditions. Thus, the present invention provides β-glucosidase polypeptide variants that have at least about 1.1-fold to about 1.5-fold, at least about 1.5-fold to about 2.5-fold, and greater than about 2.5-fold β-glucosidase activity as compared to the wild-type Bgl1 protein. Exemplary β-glucosidase polypeptide variants having improved β-glucosidase activity relative to wildtype T. aurantiacus β-glucosidase are provided herein. In some embodiments, the β-glucosidase polypeptide variants of the present invention also have improved thermoactivity, improved thermostability, and/or improved stability at low and/or high pHs relative to wildtype T. aurantiacus β-glucosidase. In some embodiments, the range of operable pH for the variant enzyme is in the range about pH 3 to about pH 8 (e.g., about pH 5). In some embodiments, the range of operable temperatures for the variant enzyme is in the range about 50 to about 80° C. (e.g., about 70° C.).

β-glucosidase activity can be determined by any suitable method(s) known in the art. In some embodiments, β-glucosidase activity is determined using a para-nitrophenyl-β-D-glucopyranoside (pNPG) assay. In some other embodiments, the β-glucosidase activity is determined using a cellobiose assay.

For example, a colorimetric pNPG (p-nitrophenyl-β-D-glucopyranoside)-based assay finds use in measuring β-glucosidase activity. In another exemplary pNPG assay, in a total volume of 100 μL, 20 μL clear media supernatant containing β-glucosidase enzyme is added to 4 mM pNPG solution in 50 mM sodium phosphate buffer at pH 6.5. The reactions are incubated at pH 6.5, 45° C. for 1 hour. The reaction mixture is quenched with 100 μL of 1M sodium carbonate pH 11 solution. The absorbance of the solution is measured at 405 nm to determine the conversion of pNPG to p-nitrophenol. The release of p-nitrophenol ($\epsilon$=17,700 $M^{-1}$ $cm^{-1}$) is measured at 405 nm to calculate β-glucosidase activity. In some embodiments, detectable β-glucosidase activity is observed under high throughput screening conditions (pH 7, 50° C.) (See e.g., Breves et al., Appl. Environ. Microbiol., 63:3902 [1997], incorporated herein by reference).

Alternatively, β-glucosidase activity may be determined using an assay which uses cellobiose as substrate. In a total volume of 100 μL, 25 μL clear media supernatant containing β-glucosidase enzyme is added to 10 g/L cellobiose (e.g., Fluka Cat. No. 22150, Sigma-Aldrich, Inc., St. Louis, Mo.) in 100 mM sodium phosphate buffer (pH 6-7) or sodium acetate buffer (pH 5-5.5). The reaction is incubated at 45-70° C. for an appropriate time (25 minutes to overnight depending on the enzyme concentration) while shaking. Glucose production is determined using an enzymatic glucose assay (e.g., K-GLUC, Megazyme, Ireland). Ten μl of each reaction is added to 190 μl GOPOD reagent (supplied as part of the K-GLUC assay kit). The reaction is incubated at 45° C. for 20 minutes and the absorbance of the solution is measured at 510 nm. The GOPOD reagent contains 50 mM potassium phosphate buffer pH7.4, 0.011M p-hydroxybenzoic acid, 0.008% w/v sodium azide, glucose oxidase (>12,000 U/L), peroxidase (>650 U/L) and 80 mg/L 4-aminoantipyrine. The glucose oxidase enzyme in the reagent reacts with any glucose present in the sample and produces hydrogen peroxide which then reacts with the 4-aminoantipyrine to produce a quinoneimine dye in quantities proportionate with the amount of glucose present and can be measured spectrophotometrically at 510 nm.

β-Glucosidase Polynucleotides and Expression Systems

The present invention provides polynucleotide sequences that encode the *T. aurantiacus* β-glucosidase variants of the invention. Genomic and cDNA *T. aurantiacus* sequences are provided herein.

In some embodiments, for expression of a β-glucosidase variant described herein, the wild-type *T. aurantiacus* cDNA sequence (SEQ ID NO:1), or the portion thereof comprising the open reading frame is used (with changes as required at codons corresponding to substitutions to produce the residue changes relative to the wild-type sequence). In addition, in some embodiments, one or more of the "silent" nucleotide changes described herein is/are incorporated.

In some other embodiments, non-naturally occurring sequences are preferred. Those having ordinary skill in the art understand that due to the degeneracy of the genetic code, a multitude of nucleotide sequences encoding β-glucosidase polypeptides of the present invention exist. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

A DNA sequence may also be designed for high codon usage bias codons (i.e., codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. In some embodiments, the DNA sequence encoding the β-glucosidase is optimized for expression in a particular host organism. Any suitable method(s) to produce optimized codons find use in the present invention. By way of illustration, but not for limitation, SEQ ID NO:7 provides a polynucleotide sequence encoding WT$^M$ (SEQ ID NO:4) designed with codon biasing for expression in *Saccharomyces cerevisiae*. Table 2 provides the codons for each of the amino acids.

TABLE 2

Amino Acids and Corresponding Codons

| Amino Acid and Abbreviations | | | Codon(s) | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |

TABLE 2-continued

Amino Acids and Corresponding Codons

| Amino Acid and Abbreviations | | | Codon(s) | | | | | |
|---|---|---|---|---|---|---|---|---|
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (See e.g., GCG CodonPreference, Genetics Computer Group Wisconsin Package; John Peden, "Codon W," University of Nottingham [1999]; McInerney, Bioinformatics 14:372-73 [1998]; Stenico et al., Nucl. Acids Res., 22:2437-46 [1994]; Wright, Gene 87:23-29 [1990]; Wada et al., Nucl. Acids Res., 20:2111-2118 [1992]; Nakamura et al., 2000, Nucl. Acids Res., 28:292; and Henaut and Danchin, in Neidhardt et al. (eds.), *Escherichia coli and Salmonella*, ASM Press, Washington D.C., [1996], p. 2047-2066, all of which are incorporated herein by reference). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTs), or predicted coding regions of genomic sequences (See e.g., Mount, *Bioinformatics: Sequence and Genome Analysis*, Cold Spring Harbor Laboratory Press, Cold Spring Harbor, N.Y., [2001], Chapter 8; Uberbacher, Meth. Enzymol. 266:259-281 [1996]; and Tiwari et al., Comput. Appl. Biosci., 13:263-270 [1997], all of which are incorporated herein by reference).

Expression Vectors

In some embodiments, the present invention makes use of recombinant constructs comprising a sequence encoding at least one β-glucosidase as described above. In some embodiments, the present invention provides an expression vector comprising at least one β-glucosidase polynucleotide operably linked to a heterologous promoter. Expression vectors of the present invention find use in transforming appropriate host cells to permit the host to express β-glucosidase protein(s). Methods for recombinant expression of proteins in fungi and other organisms are well known in the art, and a number expression vectors are available or can be constructed using routine methods as known in the art (See, e.g., Zhu et al., Plasmid 6:128-33 [2009], herein incorporated by reference).

In some embodiments, nucleic acid constructs of the present invention comprise a vector, (e.g., a plasmid, a cosmid, a phage, a virus, a bacterial artificial chromosome [BAC], a yeast artificial chromosome [YAC], etc.), into which at least one nucleic acid sequence of the present invention has been inserted. Polynucleotides of the present invention can be incorporated into any one of a variety of expression vectors suitable for expressing a polypeptide. Suitable vectors include, but are not limited to chromosomal, nonchromosomal and synthetic DNA sequences (e.g., derivatives of SV40), bacterial plasmids, phage DNA, baculovirus, yeast plasmids, vectors derived from combinations of plasmids and phage DNA, or viral DNA (e.g., vaccinia, adenovirus, fowl pox virus, pseudorabies, adenovirus, adeno-associated virus, retroviruses, etc.). Any suitable vector that transduces genetic material into a cell, and, if replication is desired, which is replicable and viable in the selected host finds use in the present invention.

In some embodiments, the construct further comprises regulatory sequences, including, for example, a promoter, operably linked to the protein encoding sequence. Large numbers of suitable vectors and promoters are known to those of skill in the art.

Promoter/Gene Constructs

As indicated above, to obtain high levels of expression in a particular host it is often useful to express *T. aurantiacus* β-glucosidase under the control of a heterologous promoter. In some embodiments, the promoter sequence is operably linked to the 5' region of the *T. aurantiacus* β-glucosidase coding sequence using routine methods.

Examples of useful promoters for expression of β-glucosidase polynucleotides include, but are not limited to promoters from fungi. For example, promoter sequences that drive expression of genes other than the β-glucosidase 1 gene in *T. aurantiacus* (e.g., a fungal promoter from a gene encoding cellobiohydrolase) find use in the present invention.

Examples of other suitable promoters useful for directing the transcription of the nucleotide constructs of the present invention in a filamentous fungal host cell include, but are not limited to the promoters obtained from the genes for *Aspergillus oryzae* TAKA amylase, *Rhizomucor miehei* aspartic proteinase, *Aspergillus niger* neutral alpha-amylase, *A. niger* acid stable alpha-amylase, *A. niger* or *Aspergillus awamori* glucoamylase (glaA), *R. miehei* lipase, *A. oryzae* alkaline protease, *A. oryzae* triose phosphate isomerase, *Aspergillus nidulans* acetamidase, and *Fusarium oxysporum* trypsin-like protease (See e.g., WO 96/00787, incorporated herein by reference), as well as the NA2-tpi promoter (a hybrid of the promoters from the genes for *A. niger* neutral alpha-amylase and *A. oryzae* triose phosphate isomerase), promoters such as cbh1, cbh2, egl1, egl2, pepA, hfb1, hfb2, xyn1, amy, and glaA (See e.g., Nunberg et al., Mol. Cell. Biol., 4:2306-2315 [1984]; Boel et al., EMBO J. 3:1581-85 [1984]; and Eur. Pat. Appln. Publ. No. 137280, all of which are incorporated herein by reference), and mutant, truncated, and hybrid promoters thereof. In yeast host cells, useful promoters include but are not limited to those from the genes for *Saccharomyces cerevisiae* enolase (eno-1), *S. cerevisiae* galactokinase (gal1), *S. cerevisiae* alcohol dehydrogenase/glyceraldehyde-3-phosphate dehydrogenase (ADH2/GAP), and *S. cerevisiae* 3-phosphoglycerate kinase. Other useful promoters for yeast host cells include those described by Romanos et al., (Romanos et al., Yeast 8:423-488 [1992], incorporated herein by reference). Promoters associated with chitinase production in fungi (e.g., *Aphanocladium album* and *Trichoderma harzianum*) also find use (See e.g., Blaiseau and Lafay, Gene 120243-248 [1992]; and Limon et al., Curr. Genet., 28:478-83 [1995], both of which are incorporated herein by reference).

Promoters known to control expression of genes in prokaryotic or eukaryotic cells or their viruses and which find use in some embodiments of the invention include, but are not limited to SV40 promoter, *E. coli* lac or trp promoter, phage lambda $P_L$ promoter, tac promoter, T7 promoter, and the like. For use in bacterial host cells, suitable promoters include, but are not limited to promoters obtained from the *E. coli* lac operon, *Streptomyces coelicolor* agarase gene (dagA), *Bacillus subtilis* levansucranse gene (sacB), *Bacillus licheniformis* alpha-amylase gene (amyl), *Bacillus stearothermophilus* maltogenic amylase gene (amyM), *Bacillus amyloliquefaciens* alpha-amylase gene (amyQ), *B. subtilis* xylA and xylB genes, and prokaryotic β-lactamase genes.

Indeed, any suitable promoter sequence that drives expression in a suitable host cell finds use in the present invention. Suitable promoter sequences can be identified using well known methods. In one approach, a putative promoter sequence is linked 5' to a sequence encoding a reporter protein, the construct is transfected into the host cell (e.g., *T. aurantiacus*) and the level of expression of the reporter is measured. Expression of the reporter can be determined by measuring, for example, mRNA levels of the reporter sequence, an enzymatic activity of the reporter protein, and/or the amount of reporter protein produced. For example, promoter activity may be determined by using the green fluorescent protein as coding sequence (See, Henriksen et al., Microbiol., 145:729-34 [1999], incorporated herein by reference) or a lacZ reporter gene (Punt et al., Gene, 197:189-93 [1997], incorporated herein by reference). Functional promoters may be derived from naturally occurring promoter sequences by directed evolution methods, using any suitable methods known in the art (See e.g. Wright et al., Hum. Gene Ther., 16:881-892 [2005], incorporated herein by reference).

Expression vectors optionally contain a ribosome binding site for translation initiation, and a transcription terminator (e.g., PinII). In some embodiments, the vector also includes appropriate sequences for amplifying expression (e.g., an enhancer).

In addition, in some embodiments, the expression vectors of the present invention contain one or more selectable marker genes to provide a phenotypic trait for selection of transformed host cells. Suitable marker genes include, but are not limited to those coding for antimicrobial resistance (e.g., resistance to ampicillin (ampR), kanamycin, chloramphenicol, tetracycline, streptomycin, spectinomycin, neomycin, geneticin, hygromycin, etc.), including but not limited to the aada gene, the streptomycin phosphotransferase (spt) gene, the neomycin phosphotransferase (nptII) gene, or the hygromycin phosphotransferase (hpt) gene. Additional selectable marker genes include, but are not limited to dihydrofolate reductase or neomycin resistance for eukaryotic cell culture, and tetracycline or ampicillin resistance in *E. coli*.

Synthesis and Manipulation of β-Glucosidase Polynucleotides

Polynucleotides encoding β-glucosidase can be prepared using any suitable method known in the art. In some embodiments, oligonucleotides of up to about 40 bases are individually synthesized, then joined (e.g., by enzymatic or chemical ligation methods, or polymerase-mediated methods) to form essentially any desired continuous sequence. In some embodiments, the polynucleotides of the present invention are prepared by chemical synthesis using, for example, classical phosphoramidite methods (See e.g., Beaucage et al., Tetrahed. Lett., 22:1859-69 [1981]; and Matthes, et al., EMBO J. 3:801-05 [1984], both of which are incorporated herein by reference). These methods are typically practiced in automated synthetic methods. For example, in the phosphoramidite method, oligonucleotides are synthesized (e.g., in an automatic DNA synthesizer), purified, annealed, ligated and cloned into appropriate vectors.

In addition, essentially any nucleic acid can be custom ordered from any of a variety of commercial sources, such as The Midland Certified Reagent Company (Midland, Tex.), The Great American Gene Company (Ramona, Calif.), ExpressGen Inc. (Chicago, Ill.), Operon Technologies Inc. (Alameda, Calif.), and many others. Thus, nucleic acids provided by these commercial companies also find use in the present invention.

It is also intended that the polynucleotides of the present invention are synthesized by suing well-known techniques (See e.g., Carruthers, et al., Cold Spring Harbor Symp. Quant. Biol., 47:411-18 [1982]; and Adams et al., J. Am. Chem. Soc., 105:661 [1983], both of which are incorporated herein by reference). In some embodiments, double stranded DNA fragments are then be obtained either by synthesizing the complementary strand and annealing the strands together under appropriate conditions, or by adding the complementary strand using DNA polymerase with an appropriate primer sequence. There are numerous texts and references known to those skilled in the art for in vitro amplification methods, including the polymerase chain reaction (PCR) and the ligase chain reaction (LCR), and many other relevant methods.

Expression Hosts

The present invention also provides engineered (recombinant) host cells transformed with an expression vector or DNA construct encoding β-glucosidase. In some embodiments, β-glucosidase expression in the cell is under the control of a heterologous promoter. In some embodiments, the host cells of the present invention are used to produce β-glucosidase polypeptides. Thus, the present invention is directed to at least one host cell comprising any β-glucosidase polynucleotide(s) of the present invention that is described. As used herein, a genetically modified or recombinant host cell includes the progeny of the host cell that comprises at least one β-glucosidase polynucleotide which encodes at least one recombinant polypeptide of the present invention. In some embodiments, the genetically modified or recombinant host cell is a microorganism. In some embodiments, the genetically modified or recombinant host cell is a prokaryote. In some embodiments, the genetically modified or recombinant host cell is a eukaryotic cell. In some embodiments, the eukaryotic host cell is a non-human cell. Suitable eukaryotic host cells include, but are not limited to, fungal cells, algal cells, insect cells, and plant cells. In some embodiments, the host cells are modified, so as to increase protein expression, secretion or stability, or to confer other desired characteristics. Cells (e.g., fungi) that have been mutated or selected to have low protease activity are particularly useful for expression. For example, in some embodiments, protease deficient strains of *T. aurantiacus* (e.g., in which the alkaline protease locus has been deleted or disrupted) find use.

Suitable fungal host cells include, but are not limited to, Ascomycota, Basidiomycota, Deuteromycota, Zygomycota, and Fungi imperfecti. In some embodiments, the fungal host cells are yeast cells or filamentous fungal cells. The filamentous fungal host cells of the present invention include all filamentous forms of the subdivision Eumycotina and Oomycota. Filamentous fungi are characterized by a vegetative mycelium with a cell wall composed of chitin, cellulose and other complex polysaccharides. The filamentous fungal host cells of the present invention are morphologically distinct from yeast. In some embodiments, the filamentous fungal host cell is a species of *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothia, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, or anamorphs, and synonyms or taxonomic equivalents thereof. However, it is not intended that the present invention be limited to any particular species of filamentous fungal host cell.

In some embodiments of the present invention, the filamentous fungal host cell is *Aspergillus* sp., *Ceriporiopsis* sp., *Chrysosporium* sp., *Corynascus* sp., *Fusarium* sp., *Humicola* sp., *Neurospora* sp., *Penicillium* sp., *Tolypocladium* sp., *Tramates* sp., or *Trichoderma* sp.

In some embodiments of the invention, the filamentous fungal host cell is a *Trichoderma* species (e.g., *T. longibrachiatum*, *T. viride* [e.g., ATCC 32098 and 32086]), *Hypocrea jecorina* or *T. reesei* (NRRL 15709, ATTC 13631, 56764, 56765, 56466, 56767 and RL-P37 and derivatives thereof; See, Sheir-Neiss et al., Appl. Microbiol. Biotechnol., 20:46-53 [1984], which is incorporated herein by reference), *T. koningii*, or *T. harzianum*. In addition, the term "*Trichoderma*" refers to any fungal strain that was previously classified, as well as those currently classified as *Trichoderma*.

In some embodiments of the present invention, the filamentous fungal host cell is an *Aspergillus* species (e.g., *A. awamori, A. funigatus, A. japonicus, A. nidulans, A. niger, A. aculeatus, A. foetidus, A. oryzae, A. sojae*, or *A. kawachi*; See e.g., Kelly and Hynes, EMBO J. 4,475479 [1985]; NRRL 3112, ATCC 11490, 22342, 44733, and 14331; Yelton et al., Proc. Natl. Acad. Sci. USA, 81, 1470-1474 [1984]; Tilburn et al., Gene 26, 205-221 [1982]; and Johnston et al., EMBO J., 4:1307-1311 [1985], all of which are incorporated herein by reference).

In some embodiments of the present invention, the filamentous fungal host cell is a *Fusarium* species (e.g., *F. bactridioides, F. cerealis, F. crookwellense, F. culmorum, F. graminearum, F. graminum. F. oxysporum, F. roseum*, or *F. venenatum*). In some embodiments of the invention, the filamentous fungal host cell is of the *Neurospora* species (e.g., *N. crassa*; See e.g., Case et al., Proc. Natl. Acad. Sci. USA, 76, 5259-5263 [1979]; U.S. Pat. No. 4,486,553; and Kinsey and Rambosek, Mol. Cell. Biol., 4:117-122 [1984], all of which are incorporated herein by reference.

In some embodiments of the present invention, the filamentous fungal host cell is a *Humicola* species (e.g., *H. insolens, H. grisea*, or *H. lanuginosa*). In some embodiments of the present invention, the filamentous fungal host cell is of a *Mucor* (e.g., *M. miehei* or *M. circinelloides*). In some embodiments of the present invention, the filamentous fungal host cell is a of the *Rhizopus* species, (e.g., *R. oryzae* or *R. niveus*). In some embodiments of the present invention, the filamentous fungal host cell is a *Penicillum* species (e.g., *P. purpurogenum, P. chrysogenum*, or *P. verruculosum*). In some embodiments of the present invention, the filamentous fungal host cell is a *Thielavia* species (e.g., *T. terrestris*). In some embodiments of the present invention, the filamentous fungal host cell is a *Tolypocladium* species (e.g., *T. inflatum* or *T. geodes*). In some embodiments of the present invention, the filamentous fungal host cell is a *Trametes* species (e.g., *T. villosa* or *T. versicolor*).

In some embodiments of the invention, the filamentous fungal host cell is a *Chrysosporium* species (e.g., *C. lucknowense, C. keratinophilum, C. tropicum, C. merdarium, C. inops, C. pannicola*, or *C. zonatum*). In some embodiments, the host cell is *C. lucknowense*.

In some embodiments of the present invention, yeast host cells find use, including, but not limited to species of *Candida, Hansenula, Saccharomyces, Schizosaccharomyces, Pichia, Kluyveromyces*, and *Yarrowia*. In some embodiments of the present invention, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

In some embodiments of the present invention, the host cell is an algal cell such as, *Chlamydomonas* (e.g., *C. Reinhardtii*) or *Phormidium* (*P. sp.* ATCC29409).

In some other embodiments, the host cell is a prokaryotic cell. Suitable prokaryotic cells include Gram-positive, Gram negative and Gram-variable bacterial cells. In some embodiments, the host cell is a species of *Agrobacterium, Alicyclobacillus, Anabaena, Anacystis, Acinetobacter, Acidothermus, Arthrobacter, Azobacter, Bacillus, Bifidobacterium, Breribacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacdlus, Lactococcus, Ilyobacter, Micrococcus, Microbacterium, Mesorhizobium, Methylobacterium, Methylobacterium, Mycobacterium, Neisseria, Pantoea, Pseudomonas, Prochlomeoccus, Rhodobacter, Rhoiopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia*, or *Zymomonas*. However, it is not intended that the host cell be limited to any particular genus or species of bacteria, as any suitable bacteria find use in the present invention.

In some embodiments, the host cell is a species of *Agrobacterium, Acinetobacter, Azobacter, Bacillus, Bifidobacterium, Buchnera, Geobacillus, Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces*, or *Zymomonas*.

In some other embodiments, the bacterial host strain is non-pathogenic to humans. In some embodiments the bacterial host strain is an industrial strain. Numerous bacterial industrial strains are known and suitable for use in the present invention. Indeed, it is intended that any suitable strain finds use in the present invention.

In some embodiments of the present invention, the bacterial host cell is an *Agrobacterium* species (e.g., *A. radiobacter, A. rhizogenes*, or *A. rubi*). In some embodiments of the present invention, the bacterial host cell is an *Arthrobacter* species (e.g., *A. aurescens, A. citreus, A. globformis, A. hydrocarboglutamicus, A. mysorens, A. nicotianae, A. paraffineus, A. protophonniae, A. roseoparqffinus, A. sulfureus*, or *A. ureafaciens*). In some additional embodiments of the present invention, the bacterial host cell is a *Bacillus* species (e.g., *B. thuringiensis, B. anthracis, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans*, or *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus*, or *B. amyloliquefaciens*). In some embodiments, the *Bacillus* host cell is *B. subtilis, B. licheniformis, B. megaterium, B. stearothermophilus*, or *B. amyloliquefaciens*. In some embodiments, the bacterial host cell is a *Clostridium* species (e.g., *C. acetobutylicum, C. tetani* E88, *C. lituseburense, C. saccharobutylicum, C. perfringens, C. thermocellum*, or *C. beijerinckii*). In some embodiments, the bacterial host cell is a *Corynebacterium* species (e.g., *C. glutamicum* or *C. acetoacidophilum*). In some embodiments the bacterial host cell is an *Escherichia* species (e.g., *E. coli*). In some embodiments, the bacterial host cell is an *Erwinia* species (e.g., *E. uredovora, E. carotovora, E. ananas, E. herbicola, E. punctata*, or *E. terreus*). In some embodiments, the bacterial host cell is of a *Pantoea* species (e.g., *P. citrea* or *P. agglomerans*). In some embodiments, the bacterial host cell is a *Pseudomonas* species (e.g., *P. putida, P. fluorescens, P. aeruginosa, P. mevalonii*, or *P. sp.* D-01 10). In some embodiments, the bacterial host cell a *Streptococcus* species (e.g., *S. equisimiles, S. pyogenes*, or *S. uberis*). In some embodiments, the bacterial host cell is a *Streptomyces* species (e.g., *S. ambofaciens, S. achromogenes, S. avermitilis, S. coelicolor, S. aureofaciens, S. aureus, S. fungicidicus, S. griseus* or *S. lividans*). In some embodiments, the bacterial host cell is a *Zymomonas* species (e.g., *Z. mobilis* or *Z. lipolytica*).

Strains that find use in the present invention including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

In some embodiments of the present invention, the host cells are genetically modified to have characteristics that improve protein secretion, protein stability or other properties desirable for expression and/or secretion of a protein. It is intended that the genetic modification be achieved by use of any suitable methods known in the art, including but not limited to genetic engineering techniques, classical microbiological techniques (e.g., chemical or UV mutagenesis and subsequent selection). In some embodiments, a combination of recombinant modification and classical selection techniques are used to produce the organism of interest. Using recombinant technology, nucleic acid molecules can be introduced, deleted, inhibited or modified, in a manner that results in increased yields of β-glucosidase within the organism or in the culture. For example, knock out of Alp1 function results in a cell that does not express most or all cellulases. Knock out of pyr5 function results in a cell with a pyrimidine deficient phenotype. These modifications and other modifications find use in the present invention.

Transformation and Culture

Any suitable method for introduction of a vector or DNA construct into a host cell find use in the present invention, including but not limited to calcium phosphate transfection, DEAE-Dextran mediated transfection, electroporation, or other common techniques known in the art.

In some embodiments of the present invention, the engineered host cells are cultured in conventional nutrient media modified as appropriate for activating promoters, selecting transformants, and/or amplifying the β-glucosidase polynucleotide. Culture conditions, such as temperature, pH and the like, are those previously used with the host cell selected for expression, and will be apparent to those skilled in the art. Many references are known to those skilled in the art and are available for the culture and production of many cells, including cells of bacterial, plant, animal (especially mammalian) and archebacterial origin.

In some embodiments of the present invention, host cells expressing the β-glucosidase polypeptides of the present invention are grown under batch or continuous fermentations conditions. Classical "batch fermentation" is a closed system, wherein the composition of the medium is set at the beginning of the fermentation and is not subject to artificial alterations during the fermentation period. A variation of the batch system is a "fed-batch fermentation" which also finds use in the present invention. In the fed-batch system, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. "Continuous fermentation" is an open system where a defined fermentation medium is added continuously to a bioreactor and an equal amount of conditioned medium is removed simultaneously for processing. Continuous fermentation generally maintains the cultures at a constant high density in which the cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments of the present invention, cell-free transcription/translation systems are employed to produce β-glucosidase polypeptides using the polynucleotides of the present invention. Several such systems are commercially available and are well-known to those in the art.

Production and Recovery of β-Glucosidase Polypeptides

The present invention provides methods of making polypeptides having β-glucosidase activity. In some embodiments, the methods comprise providing a host cell transformed with any one or more) of the described β-glucosidase polynucleotides of the present invention; culturing the transformed host cell in a culture medium under conditions in which the host cell expresses the encoded β-glucosidase polypeptide(s); and optionally recovering or isolating the expressed β-glucosidase polypeptide(s), or recovering or isolating the culture medium containing the expressed β-glucosidase polypeptide(s). In some embodiments of the present invention, the methods further provide the step of lysing the transformed host cells after expressing the encoded β-glucosidase polypeptide(s). In some embodiments, after the transformed cells are lysed, the expressed β-glucosidase polypeptide(s) is/are recovered or isolated from the cell lysate. The present invention further provides methods of making at least one β-glucosidase polypeptide, comprising cultivating a host cell transformed with at least one β-glucosidase polynucleotide under conditions suitable for the production of at least one β-glucosidase polypeptide and recovering at least one of the produced β-glucosidase polypeptides.

In some embodiments, recovery or isolation of the β-glucosidase polypeptide(s) is from the host cell culture medium, the host cell or both, using protein recovery techniques that are well known in the art, including those described herein. In some embodiments, the cells are harvested by centrifugation, disrupted by physical or chemical means, and the resulting crude extract is retained for further purification. It is contemplated that any methods suitable for disrupting the cells expressing the β-glucosidase polypeptide(s) find use in the present invention, including but not limited to freeze-thaw cycling, sonication, mechanical disruption, or use of cell lysing agents, or other methods, which are well known to those skilled in the art.

In some embodiments of the present invention, the resulting polypeptide(s) is/are recovered/isolated and optionally purified by any of a number of methods known in the art. For example, in some embodiments, the polypeptide(s) is/are isolated from the nutrient medium by conventional procedures including, but not limited to, centrifugation, filtration, extraction, spray-drying, evaporation, chromatography (e.g., ion exchange, affinity, hydrophobic interaction, chromatofocusing, and/or size exclusion), and/or precipitation. In some embodiments, protein refolding steps are used, as desired/needed to obtain the correct conformation of the polypeptide(s). In addition, in some embodiments, high performance liquid chromatography (HPLC) is employed in the final purification steps (See e.g., Parry et al., Biochem. J., 353:117 [2001]; and Hong et al., Appl. Microbiol. Biotechnol. 73:1331 [2007], both of which are incorporated herein by reference). There are a variety of purification methods known in the art and any suitable method finds use in the present invention.

In some embodiments, immunological methods are used to purify β-glucosidase polypeptides. In some embodiments, antibody raised against at least one β-glucosidase polypeptide (e.g., against a polypeptide comprising SEQ ID NO:2 or an immunogenic fragment thereof) using conventional methods is immobilized on beads, mixed with cell culture media under conditions in which the β-glucosidase is bound, and precipitated. In some other embodiments, immunochromatography finds use.

In some embodiments of the present invention, the β-glucosidase is expressed as a fusion protein including a non-enzyme portion. In some embodiments, the β-glucosidase sequence is fused to a purification facilitating domain. As used herein, the term "purification facilitating domain" refers to a domain that mediates purification of the polypeptide to which it is fused. Suitable purification domains include, but are not limited to metal chelating peptides, histidine-tryptophan modules that allow purification on immobilized metals, a sequence which binds glutathione (e.g., GST), a hemagglutinin (HA) tag (i.e., corresponding to an epitope derived from the influenza hemagglutinin protein; Wilson et al., Cell 37:767 [1984]), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the β-glucosidase polypeptide is useful to facilitate purification. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography; See e.g., Porath et al., Prot. Express. Purific., 3:263-281 [1992]) while the enterokinase cleavage site provides a means for separating the β-glucosidase polypeptide from the fusion protein. pGEX vectors (Promega; Madison, Wis.) also find used in expressing the fusion polypeptides of the present invention with glutathione S-transferase (GST). In general, these fusion proteins are soluble and can easily be purified from lysed cells by adsorption to ligand-agarose beads (e.g., glutathione-agarose in the case of GST-fusions) followed by elution in the presence of free ligand.

Methods of Using β-Glucosidase Polypeptides and Cells Expressing β-Glucosidase Polypeptides As described herein, β-glucosidase polypeptides of the present invention find use in catalyzing the hydrolysis of a sugar dimer with the release of the corresponding sugar monomer (e.g., the conversion of cellobiose with the release of glucose). Thus, the present invention provides methods for producing glucose by (a) providing a cellobiose; and (b) contacting the cellobiose with at least one β-glucosidase polypeptide of the present invention under conditions sufficient to form a reaction mixture for converting the cellobiose to glucose. In some embodiments, a β-glucosidase polypeptide is utilized in such methods in isolated form, while in other embodiments, at least one β-glucosidase polypeptide is/are used as part of a composition. In some embodiments, the β-glucosidase polypeptide is provided in cell culturing media or in a cell lysate. In some embodiments, after the β-glucosidase polypeptide is produced by culturing a host cell transformed with a β-glucosidase polynucleotide or vector of the present invention, the β-glucosidase need not be isolated from the culture medium (i.e., if the β-glucosidase is secreted into the culture medium) or cell lysate (i.e., if the β-glucosidase is not secreted into the culture medium) or used in purified form to be useful in further methods of using the β-glucosidase polypeptide. It is intended that any composition, cell culture medium, or cell lysate containing at least one β-glucosidase polypeptide of the present invention is suitable for use in methods that utilize a β-glucosidase. Therefore, the present invention further provides a method for producing glucose, by: (a) providing a cellobiose; and (b) contacting the cellobiose with a culture medium or cell lysate or composition comprising at least one β-glucosidase polypeptide of the present invention under conditions sufficient to form a reaction mixture for converting the cellobiose to glucose.

The present invention further provides compositions that are useful for the enzymatic conversion of cellobiose to glucose. For example, in some embodiments of the present invention, one or more β-glucosidase polypeptides are combined with at least one additional enzyme and/or an agent that alters the bulk material handling properties or further processability of the β-glucosidase(s) (e.g., a flow-aid agent, water, buffer, surfactant, etc.) or that improves the efficiency of the conversion of cellobiose to glucose, as described herein. In some embodiments, the additional enzyme is a different β-glucosidase, while in other embodiments, it is another cellulase or an enzyme from a different class (e.g., an amylase, etc.).

Cellulase Mixtures

In some embodiments of the present invention, at least one of the β-glucosidases provided herein is combined with other cellulases to form a cellulase mixture. In some embodiments, the cellulase mixture comprises cellulases selected from CBH, EG and BG cellulases (e.g., cellulases from *Trichoderma reesei* (e.g., C2730 cellulase from *Trichoderma reesei* ATCC No. 25921 available from Sigma-Aldrich, Inc.; and C9870 ACCELLERASE™ 1500, available from Genencor), *Acidothermus cellulolyticus*, *Thermobifida fusca*, *Humicola grisea* and *Chrysosporium* sp.). The enzymes of the cellulase mixture work together to decrystallize and hydrolyze the cellulose in biomass substrates to yield soluble sugars, including, but not limited to glucose.

Cellulase mixtures for efficient enzymatic hydrolysis of cellulose are known (See e.g., Viikari et al., Adv. Biochem. Eng. Biotechnol., 108:121-45, [2007]; and US Pat. Appln. Publns. US 2009/0061484; US 2008/0057541; and US 2009/0209009; each of which is incorporated herein by reference). In some embodiments, mixtures of purified naturally occurring or recombinant enzymes are combined with cellulosic feedstock or a product of cellulose hydrolysis. Alternatively or in addition, one or more naturally occurring or recombinant cellulases, each producing one or more naturally occurring or recombinant cellulases, may be combined with cellulosic feedstock or a product of cellulose hydrolysis.

Other Components of β-Glucosidase Compositions

In some embodiments, the β-glucosidase polypeptides of the present invention are used in compositions comprising combinations of the polypeptides with other optional ingredients such as buffer(s), surfactant(s), and/or scouring agent(s). In some embodiments, at least one buffer is used with a β-glucosidase polypeptide of the present invention (optionally combined with other cellulases, including another β-glucosidase and/or other enzymes) in order to maintain a desired pH within the solution in which the β-glucosidase is employed. The exact concentration of buffer employed will depend on several factors which the skilled artisan can determine Suitable buffers are well known in the art. In some embodiments, at least one surfactant is used in combination with the β-glucosidases of the present invention. Suitable surfactants include any surfactant compatible with the β-glucosidase and optionally, any other cellulases and/or enzymes being used. Exemplary surfactants include, but are not limited to anionic, non-ionic, and ampholytic surfactants.

Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, etc. Suitable counter ions for anionic surfactants include but are not limited to alkali metal ions (e.g., sodium and potassium); alkaline earth metal ions (e.g., calcium and magnesium); ammonium ion; and alkanolamines having from 1 to 3 alkanol groups of carbon number 2 or 3. Ampholytic surfactants suitable for use in the practice of the present invention include, but are not limited to quaternary ammonium salt sulfonates, betaine-type ampholytic surfactants, etc. Suitable nonionic surfactants include, but are not limited to polyoxalkylene ethers, as well as higher fatty acid alkanolamides or alkylene oxide adducts thereof, fatty acid glycerine monoesters, etc. In some embodiments, mixtures of surfactants (e.g., those well known in the art) find use in the present invention.

Production of Fermentable Sugars from Cellulosic Biomass

In some embodiments of the present invention, β-glucosidase polypeptides of the present invention, as well as any composition, culture medium, or cell lysate comprising such β-glucosidase polypeptides, are used in the production of monosaccharides, disaccharides, or oligomers of a mono- or di-saccharide as chemical or fermentation feedstock from biomass. As used herein, the term "biomass" refers to living or dead biological material that contains a polysaccharide substrate (e.g., cellulose, starch, etc.). Therefore, the present invention provides methods for converting a biomass substrate to a fermentable sugar, the methods comprising contacting a culture medium or cell lysate containing at least one β-glucosidase polypeptide of the present invention with the biomass substrate, under conditions suitable for the production of the fermentable sugar. The present invention further provides methods of converting a biomass substrate to a fermentable sugar by (a) pretreating a cellulose substrate to increase its susceptibility to hydrolysis; (b) contacting the pretreated cellulose substrate of step (a) with a composition, culture medium or cell lysate containing at least one β-glucosidase polypeptide of the present invention (and optionally other cellulases and/or other enzymes) under conditions suitable for the production of the fermentable sugar.

In some embodiments of the present invention, the biomass includes, but is not limited to cellulosic substrates including but not limited to, wood, wood pulp, paper pulp, corn stover, corn fiber, rice, paper and pulp processing waste, woody or herbaceous plants, fruit or vegetable pulp, distillers grain, grasses, rice hulls, wheat straw, cotton, hemp, flax, sisal, corn cobs, sugar cane bagasse, switch grass and mixtures thereof. In some embodiments, the biomass is pretreated to increase the susceptibility of cellulose to hydrolysis using methods known in the art such as chemical, physical and biological pretreatments (e.g., steam explosion, pulping, grinding, acid hydrolysis, solvent exposure, etc., as well as combinations thereof). In some embodiments, the biomass comprises transgenic plants that express ligninase and/or cellulase enzymes which degrade lignin and cellulose (See e.g., US Pat. Appln. Publn. No. 2008/0104724, which is incorporated herein by reference).

In some embodiments, the β-glucosidase polypeptide(s), β-glucosidase polypeptide-containing compositions, cell culture media, and/or cell lysates are reacted with the biomass or pretreated biomass at a temperature in the range of about 25° C. to about 100° C., about 30° C. to about 90° C., about 30° C. to about 80° C., about 40° C. to about 80° C. and about 35° C. to about 75° C. Also, the biomass may be reacted with the β-glucosidase polypeptides, β-glucosidase polypeptide-containing compositions, cell culture media, and/or cell lysates at a temperature about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C., or at about 100° C. In addition to the temperatures described above, conditions suitable for converting a biomass substrate to a fermentable sugar that employ at least one β-glucosidase polypeptide of the present invention (optionally in a composition, cell culture medium, or cell lysate) include carrying out the process at a pH in a range from about pH 3.0 to about 8.5, about pH 3.5 to about 8.5, about pH 4.0 to about 7.5, about pH 4.0 to about 7.0 and about pH 4.0 to about 6.5. Those having ordinary skill in the art appreciate that the reaction times for converting a particular biomass substrate to a fermentable sugar may vary, but the optimal reaction time can be readily determined Exemplary reaction times include, but are not limited to those in the range of from about 1 to about 240 hours, from about 5 to about 180 hrs, and from about 10 to about 150 hrs. For example, the incubation time may be at least 1 hr, at least 5 hrs, at least 10 hrs, at least 15 hrs, at least 25 hrs, at least 50 hr, at least 100 hrs, at least 180 etc. (i.e., any suitable incubation time for the particular system in use.

In some embodiments, reaction of the β-glucosidase with biomass substrate or pretreated biomass substrate under these conditions results in the release of substantial amounts of the soluble sugars from the substrate. For example in some embodiments, at least 20%, at least 30%, at least 40%, at least 50%, at least 60%, at least 70%, at least 80%, at least 90%, or more soluble sugars are available, as compared to the release of sugar by the wildtype T. aurantiacus. In some embodiments, the amount of soluble sugars made available is at least 2-fold, at least 3-fold, at least 4-fold, or at least 5-fold greater than that made available by the wildtype T. aurantiacus under the same conditions. In some embodiments, the soluble sugars comprise glucose.

In some embodiments, the soluble sugars produced by the methods of the present invention are used to produce at least one alcohol (e.g., ethanol, butanol, etc.). The present invention therefore provides methods of producing at least one alcohol, wherein the method comprises: (a) providing a fermentable sugar produced using at least one β-glucosidase polypeptide of the present invention in the methods described herein; (b) contacting the fermentable sugar with a fermenting microorganism to produce at least one alcohol and/or other metabolic product; and (c) recovering at least one alcohol and/or other metabolic product.

In some embodiments, at least one β-glucosidase polypeptide of the present invention, β-glucosidase polypeptide-containing composition, cell culture medium, and/or cell lysate containing the β-glucosidase polypeptide is used to catalyze the hydrolysis of a biomass substrate to a fermentable sugar in the presence of a fermenting microorganism such as a yeast (e.g., *Saccharomyces* sp., such as *S. cerevisiae*; *Pichia* sp.; etc.) or other C5- or C6-fermenting microorganisms that are well known in the art (e.g., *Zymomonas* sp., *E. coli*, etc.), to produce an end-product such as ethanol. In methods involving simultaneous saccharification and fermentation (SSF) processes, the fermentable sugars (e.g., glucose and/or xylose) are removed from the system by the fermentation process.

The soluble sugars produced by the use of a β-glucosidase polypeptide of the present invention also find use in the production of other end-products (e.g., acetone, amino acids [e.g., glycine, lysine, etc.], organic acids [e.g., lactic acid, etc.], glycerol, diols [e.g., 1,3 propanediol, butanediol, etc.], and animal feed.

Those of skill in the art will readily appreciate that the β-glucosidase polypeptide compositions of the present invention also find use in the form of an aqueous solution or a solid concentrate. In some embodiments, when aqueous solutions are employed, the β-glucosidase concentrate solution is diluted to allow accurate concentrations for the use intended. The concentrate is provided in any suitable form (e.g., those recognized in the art including, but not limited to liquids, emulsions, suspensions, gel, pastes, granules, powders, agglomerates, solid disks, etc.). In some embodiments, additional materials are also be used with or included in the β-glucosidase compositions of the present invention as desired, including but not limited to stones, pumice, fillers, solvents, enzyme activators, and anti-redeposition agents, etc., depending on the intended use for the composition.

The β-glucosidase polypeptides and compositions provided by the present invention also find use in the food and beverage industry, for example, in the process of wine making for the efficient release of monoterpenols (See e.g., Yanai and Sato, Am. J. Enol. Eitic., 50:231-235 [1999], which is incorporated herein by reference) and for the preparation of glycon isoflavone-enriched tofu (See e.g., Mase et al., J. Appl. Glycosci., 51:211-216 [2004], which is incorporated herein by reference). The β-glucosidase polypeptides of the present invention also find use in detergent compositions for improved cleaning performance (See e.g., U.S. Pat. Nos. 7,244,605, and 5,648,263; and WO 2004/048592, all of which are incorporated herein by reference).

The foregoing and other aspects of the invention may be better understood in connection with the following non-limiting examples. The present invention is described in further detail in the following Examples which are not in any way intended to limit the scope of the invention as claimed.

EXPERIMENTAL

In the experimental disclosure which follows, the following abbreviations apply: WT and wt (wild-type); ppm (parts per million); M (molar); mM (millimolar); .mu.M (micromolar); nM (nanomolar); mol (moles); mmol (millimoles); μmol and umol (micromoles); nmol (nanomoles); gm (grams); mg (milligrams); .mu.g (micrograms); pg (picograms); L (liters); ml and mL (milliliters); μl and uL (microliters); cm (centimeters); mm (millimeters); μm and um (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); rpm (revolutions per minute); $H_2O$ (water); $dH_2O$ (deionized water); (HCl (hydrochloric acid); aa (amino acid); by (base pair); kb (kilobase); kbp (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); xg (times gravity); OD (optical density); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PCR (polymerase chain reaction); SDS (sodium dodecyl sulfate); Tris (tris(hydroxymethyl)aminomethane); HPLC (high pressure liquid chromatography); RP-HPLC (reverse phase high pressure liquid chromatography); ATCC (American Type Culture Collection, Rockville, Md.); Gibco/BRL (Gibco/BRL, Grand Island, N.Y.); Sigma (Sigma Chemical Co., St. Louis, Mo.); Gene Oracle (Gene Oracle, Inc., Mountain View, Calif.); USBio (United States Biological, Swampscott, Mass.); Sartorius (Sartorius Stedim Biotech, Division of Sartorius AG, Goettingen, Germany); Eppendorf (Eppendorf North America, Westbury, N.Y.); Phenomenex (Phenomenex, Inc., Torrance, Calif.); FMC (FMC Corporation, Philadelphia, Pa.); Difco (Difco Laboratories, Detroit, Mich.); Molecular Devices (Molecular Devices, Corp., Sunnyvale, Calif.); Fluka (Fluka Chemie AG, Buchs, Switzerland).

Example 1

Wild-type *T. aurantiacus* Bgl1 Gene Acquisition and Construction of Expression Vector The secreted form of the *T. aurantiacus* Bgl1 protein ("Bgl1 WT"; SEQ ID NO:2) was used to design a synthetic nucleotide sequence based on codon selection from a merged *S. cerevisiae* and *P. pastoris* codon bias table and excluding BamHI, SalI, SfiI, BglI, NgoMIV, and SpeI restriction sites. In addition, an amino terminal methionine residue was added ("Bgl1 $WT^M$"; SEQ ID NO:4). The Bgl1 $WT^M$ encoding sequence was synthesized by Gene Oracle and expression constructs were prepared in which the Bgl1 $WT^M$ sequence was linked to a yeast or fungal signal peptide appropriate for secretion in *S. cerevisiae*. The signal peptide sequences were added by PCR primer overlap extension. The Bgl1 construct was cloned into a pYT72 shuttle vector (i.e., pBS24Ub modified so that transcription is under the control of an *S. cerevisiae* adh2 promoter; See e.g., Sabin et al., BioTechnol., 7:705 [1989]).

*S. cerevisiae* cells were transformed with the expression vectors. Clones with β-glucosidase activity were identified on agar plates containing 50 μg/ml X-glucoside (5-bromo-4-chloro-3-indolyl-β-D-glucopyranoside; Sigma) and sequences from the transformants were verified.

Example 2

Production of β-Glucosidase Powders—Shake Flask Procedure

A single colony of *S. cerevisiae* containing a plasmid encoding Bgl1 $WT^M$ was inoculated into 3 ml of synthetic defined medium containing 60 g/L glucose, 6.7 g/L yeast nitrogen base, 5 g/L ammonium sulfate, and 2 g/L amino acid drop-out mix minus uracil (USBio #D9535). Cells were grown overnight (at least 16 hrs) in an incubator at 30° C. with shaking at 250 rpm. Then, 1 ml of this culture was diluted into 25 ml synthetic defined medium containing 20 g/L glucose, 6.7 g/L yeast nitrogen base, 5 g/L ammonium sulfate, and 2 g/L amino acid drop-out mix minus uracil (USBio #D9535) in a 250 ml flask. This culture was incubated for 72 hours at 30° C., while shaking at 250 rpm. Cells were harvested by centrifugation (3000×g, 15 minutes, 5° C.). The supernatant was decanted into a new tube and concentrated 10 fold using a centrifugal concentrator (VIVASPIN20; Sartorius). The activity of the $WT^M$ Bgl1 was confirmed using pNPG (p-nitrophenyl-β-D-glucopyranoside) as substrate using the method described by Hong et al., (Hong et al., Appl. Environ. Microbiol., 73:1331 [2007], incorporated herein by reference).

Example 3

Assays to Determine β-Glucosidase Activity

This Example describes three assays used to determine the presence or activity of β-glucosidase.
A.  5-bromo-4-chloro-3-indolyl-beta-d-glucopyranoside (X-glu) Assay
Petri plates containing Synthetic Defined medium (SD-ura; comprising 20 g/L glucose, 6.7 g/L yeast nitrogen base, 5 g/L ammonium sulfate, 2 g/L amino acid drop-out mix minus uracil (USBio D9535), 15 g/L agar and 40 mg/L 5-bromo-4-chloro-3-indolyl-beta-d-glucopyranoside) were made. *S. cerevisiae* containing a plasmid with the bgl1 gene were plated onto these plates and incubated at 30° C. for 3 days. All of the colonies observed in the plates turned a blue color, indicating that organisms were producing an active β-glucosidase which hydrolyses the X-glu to release a chromophore. The negative control consisting of *S. cerevisiae* transformed with an empty vector produced white colonies.
B. Para-nitrophenyl Glucoside (pNPG) Assay
In a total volume of 100 μl, 30 μl concentrated supernatant from Example 2 was added to 4 mM pNPG (Fluka) in a solution containing 25 mM sodium acetate, pH 5. The reaction was shaken for 30 min at 50° C. and subsequently 100 μl of 2 M KCO3 was added to terminate the reaction. The liberated p-nitrophenol was measured spectrophotometrically at 405 nm with a Spectramax 190, (Molecular Devices) and the amount of released p-nitrophenol was calculated from absorbance at 405 nm., using methods known in the art (See e.g., Hong et al., Appl. Environ. Microbiol., 73:1331 [2007]).

When the wild-type ($WT^M$) enzyme produced as described in Example 2, was reacted with pNPG, the resulting mixture produced an absorbance of 4. This was indicative of a saturating level of activity. The negative control consisting of *S. cerevisiae* transformed with an empty vector produced an absorbance of 0-0.1 under the same reaction conditions.
C. Cellobiose Assay
Activity on substrate cellobiose was determined using a reaction mixture of a 100 μl volume containing 20 μl culture supernatant, 10 g/L cellobiose, (Fluka Cat. No. 22150) and 25 mM sodium acetate, pH 5. The reactions were incubated at 60° C. for an appropriate time (1 hour to overnight depending on the enzyme concentration and activity) while shaking, quenched with equal volume of 10 mM sulfuric acid and mixed well. Then, 150 μl of the reaction was filtered through a 0.4 μm filter (filter plates were used) through centrifugation at 2000 rpm (Eppendorf, centrifuge model No. 5810R (15 amps)) for 2 min. Glucose production and/or cellobiose depletion was tracked through HPLC analysis using a PHENOMENEX® Rezex RHM-monosaccharide 150*7.8 mm (005-0132-KO) HPLC with guard column (Phenomenex). The mobile phase was water at a flow rate of 1 ml/min. The column was used at a temperature of 50° C., typical sample injection volume was 20 µl, and run time was 3.8-4 min. Peak areas were quantified according to calibration curves with glucose and cellobiose as standards in the range of 1-73 mM. Typical retention time observed for cellobiose and glucose were 2.85 and 3.5 min, respectively.

Example 4

Characterization of Recombinant *T. aurantiacus* Bgl1

The pH dependency of *S. cerevisiae*-produced *T. aurantiacus* Bgl1 was determined by measuring its activity in a cellobiose assay at pH 2, 3, 3.5, 4, 4.5, 5, 5.5, 6, 6.5, 7, 7.5 and 8. Experiments were conducted at 50° C. with 10 g/L of cellobiose for 90 minutes with 25 mM buffer (phosphate for pH 2, sodium citrate for the pH range 3-3.5, sodium acetate for pH range 4-5.5, and phosphate for pH range 6-8). The range of operable pH for the enzyme was found to be between pH 3-8. The optimal activity was measured at pH 5, in agreement with prior studies (See e.g., Hong et al., Appl. Microbiol. Biotechnol., 73:1331 [2007]).

The temperature dependency of *S. cerevisiae*-produced *T. aurantiacus* Bgl1 was determined by measuring its activity in a cellobiose assay at temperatures between 30° C. and 95° C. Experiments were conducted in pH 5 acetate buffer in the presence of 10 g/L cellobiose for 60 minutes. Eznymatic activity was determined as the proportion of initial cellobiose converted to the product. The range of operable temperatures for the Bgl1 wild-type enzyme was determined to be between 50-80° C. The optimal temperature for the *S. cerevisiae*-produced *T. aurantiacus* Bgl1 was 70° C., in agreement with prior studies (See e.g., Hong et al., Appl. Microbiol. Biotechnol., 73:1331 [2007]).

Example 5

High Throughput Assays to Identify *T. aurantiacus* β-Glucosidase Variant Polypeptides with Improved Properties Libraries of cells producing *T. aurantiacus* β-glucosidase variant polypeptides were obtained using mutagenesis and directed evolution methods. Individual yeast cells were cloned and grown on X-glu plates as described in Example 2. Blue colonies were picked and cultured as described in Example 2 with the following exceptions. The initial growth was done in 250 µl, and the expression was done in a 350 µl volume. Upon expression, cells supernatants were used to assay for enzyme activities.

The supernatants were screened and evaluated for improvements over the wild-type *T. aurantiacus* Bgl1, using the cellobiose assay of Example 3. These assays were performed as described in Example 3 with the following exceptions. The cellobiose reactions were performed with 20 µl enzyme, at 60° C., with 3.3 g/L cellobiose. Glucose was added to the reaction at a final concentration of 50 g/L. The reaction time for each assay was optimized before screening using 25 mM sodium acetate containing 0.125 mg/ml bovine serum albumin (BSA), pH 5, to dilute the enzyme. The dilution level typically was between 1-4 fold.

Example 6

Improved β-Glucosidase Activities of Engineered *T. aurantiacus* β-Glucosidase Variant Polypeptides Tables 6-1 and 6-2 show the improvement in activities of exemplary *T. aurantiacus* β-glucosidase variant polypeptides encompassed by the invention, and their activities for converting cellobiose to glucose (as fold improvements over the $WT^M$ enzyme activity measured under similar conditions) using the cellobiose assay described in Example 3. In these Tables, activity is described as the fold improvement ("FI") over the enzyme ($WT^M$; SEQ ID NO:4).

TABLE 6-1

Improved β-Glucosidase Variant Polypeptides Derived From the *T. aurantiacus* Bgl1 Wildtype Enzyme

| Ref. | Substitutions* | "Silent" Base Changes** | FI | Signal Peptide |
|---|---|---|---|---|
| TaB1 | $WT^M$ | | | Yeast |
| TaB2 | T151S, Y642N, N651K | | ++ | Yeast |
| TaB3 | D204G, K292I, E345V, Y747C | t1044c, t1656a, t2052c | + | Yeast |
| TaB4 | H685Y, P791T | a2520g | + | Yeast |

TABLE 6-2

Improved β-Glucosidase Variant Polypeptides Derived From the *T. aurantiacus* Bgl1 Wildtype Enzyme

| Ref. | Substitutions* | "Silent" Base Changes** | FI | Signal Peptide |
|---|---|---|---|---|
| TaB5 | $WT^M$ | | | fungal |
| TaB6 | T151S, Y642N, N651K | | ++ | fungal |
| TaB7 | K101R, T151S, K343R, N356S, S409N, Y642N, N651K | | ++*** | fungal |
| TaB8 | K101R, T151S, K343R, N356S, S409N, Y642N, N651K | a1515g | ++ | fungal |
| TaB9 | M1T, K55R, K101R, T151S, R331K, Y332C, K343R, N356S, S409N, Y642N | | ++ | fungal |
| TaB10 | M1T, K101R, T151S, K292E, K343R, S409N, Y642N, P740S | | +++ | fungal |
| TaB11 | M1T, T151S, K343R, S409N, A479V, Y642N, Y680F | g165a | +++ | fungal |
| TaB12 | L150V, T151S, K343R, S409N, K457R, Y642N, N651K | t651c, t726c | +++ | fungal |
| TaB13 | S87N, T151S, F288Y, Y642N, N651K | | +++ | fungal |

Key to Tables 6-1 and 6-2

"+" indicates a fold improvement (FI) of 1.0 to 1.5.

"++" indicates a FI of greater than 1.5 to 2.5.

"+++" indicates a FI of greater than 2.5.

* Residue numbering refers to SEQ ID NO: 4.

** Base numbering refers to SEQ ID NO: 3.

*** Variant was not improved over $WT^M$ after retransformation.

Example 7

Glucose Production by Variant TaB6

Variant TaB6 was shown to produced glucose from AVICEL® cellulose when tested with 1 g/L C1 cellulase and 5 g/L TaB6 Bgl1 variant (see FIG. 1). Experiments were conducted with 20% AVICEL® cellulase, at pH 5, 65° C., for 48 h, while shaking at 200 rpm. Glucose production and/or cellobiose depletion was tracked through HPLC analysis using a PHENOMENEX® Rezex RHM-monosaccharide 150*7.8 mm (005-0132-KO) HPLC with guard column (Phenomenex, Inc., Torrance, Calif.). The mobile phase that was used was water at a flow rate of 1 ml/min. The column was used at a temperature of 50° C., typical sample injection volume was 20 µl, and run time was 3.8-4 min Peak areas were quantified according to calibration curves with glucose and cellobiose as standards in the range of 1-73 mM. Typical retention time observed for cellobiose and glucose were 2.85 and 3.5 min, respectively.

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

---

We claim:

1. A recombinant variant β-glucosidase, comprising a substitution set selected from the group consisting of: T151S-Y642N-N651K, K101R-T151S-K343R-N356S-S409N-Y642N-N651K, M1T-K55R-K101R-T151S-R331K-Y332C-K343R-N356S-S409N-Y642N, M1T-K101R-T151S-K292E-K343R-S409N-Y642N-P740S, M1T-T151S-K343R-S409N-A479V-Y642N-Y680F, L150V-T151S-K343R-S409N-K457R-Y642N-N651K, and S87N-T151S-F288Y-Y642N-N651K of SEQ ID NO: 4, wherein said recombinant variant β-glucosidase has greater enzymatic activity than the amino acid sequence of SEQ ID NO: 4.

2. The recombinant variant β-glucosidase of claim 1, wherein the polynucleotide sequence encoding said variant comprises a polynucleotide sequence having at least one base change selected from t1044c, t1656a, t2052c, and/or a2520g wherein said bases are found in the polynucleotide sequence of SEQ ID NO: 3.

3. A composition comprising the recombinant variant β-glucosidase of claim 1.

4. The composition of claim 3, further comprising at least one additional enzyme.

5. The composition of claim 4, wherein said at least one additional enzyme is a cellulase.

6. The composition of claim 4, wherein said at least one additional enzyme is an additional recombinant variant β-glucosidase of SEQ ID NO: 4.

* * * * *